United States Patent [19]

Peck

[11] Patent Number: 5,211,827

[45] Date of Patent: May 18, 1993

[54] ELECTROCHEMICAL CELL WITH IONIC SEMICONDUCTOR SEPARATOR

[75] Inventor: Robert L. Peck, Lebanon, Conn.

[73] Assignee: T and G Corporation, Lebanon, Conn.

[21] Appl. No.: 740,061

[22] Filed: Aug. 5, 1991

Related U.S. Application Data

[60] Division of Ser. No. 542,304, Jun. 22, 1990, Pat. No. 5,055,171, which is a continuation-in-part of Ser. No. 275,977, Nov. 25, 1988, abandoned, which is a continuation-in-part of Ser. No. 915,994, Oct. 6, 1986, Pat. No. 4,797,190.

[51] Int. Cl.$^5$ ............................................. C25B 13/08
[52] U.S. Cl. ................................. 204/252; 204/296; 524/507; 524/510; 524/520; 524/521; 524/522; 524/502
[58] Field of Search ............................... 204/252, 296; 252/315.011

[56] References Cited

U.S. PATENT DOCUMENTS

| | | | |
|---|---|---|---|
| 3,284,238 | 11/1966 | White | 429/33 |
| 3,629,087 | 12/1971 | Rubin | 204/181 |
| 4,885,077 | 12/1989 | Karakelle et al. | 204/403 |

*Primary Examiner*—John Niebling
*Assistant Examiner*—Kathryn Gorgos
*Attorney, Agent, or Firm*—Chilton, Alix & Van Kirk

[57] ABSTRACT

An electrochemical cell employs an ionic semiconductor material as a separator between an anolyte and a catholyte. ionic semiconductor material includes 10 to approximately 50 percent by weight of a hydrogel which is dispersed within an inert nonporous matrix material to form a composite wherein the quantity of water that can be absorbed by the composite does not substantially exceed the weight of the composite.

5 Claims, 1 Drawing Sheet

ELECTROCHEMICAL CELL WITH IONIC SEMICONDUCTOR SEPARATOR

CROSS-REFERENCE TO RELATED APPLICATION

This application is a divisional of copending application Ser. No. 542,304 filed on Jun. 22, 1990, now U.S. Pat. No. 5,055,171, which is a continuation-in-part of application Ser. No. 275,977 filed Nov. 25, 1988, now abandoned. Application Ser. No. 275,977 was a continuation-in-part of application Ser. No. 915,994 filed Oct. 6, 1986, now U.S. Pat. No. 4,797,190.

BACKGROUND OF THE INVENTION (1) Technical Field of the Invention

This invention relates to nonporous and non-diffusive, polymeric ionic semiconductor materials which can function as novel highly selective permeable membranes driven by ionic depletion gradients and to a method for making such membranes. More particularly, the present invention is directed to materials which have isolated catenated water molecules formed on dispersed and bound hydrogel molecules contained within an inert nonporous nonpermeable matrix, such materials thus having the apparent ability to split water into its constituent ions, and their application as a pervaporative material or in keeping two electrolytes separate while transferring specific ions. The invention is also directed to methods and materials for use in the establishment of reversible chemical-electrical/electrical-chemical energy conversions. Accordingly, the general objects of this invention are to provide novel and improved methods, materials and apparatus of such character.

(2) Description of the Prior Art

Proton selective transport membranes have been of general interest for a number of years since many electrochemical half-cell reactions can be linked with a proton exchange. One of the first known uses of a proton selective membrane was in an early battery known as the Daniell cell. The Daniell cell utilized two separate electrolytes and electrodes, e.g., $Zn/ZnSO_4$ and $CuSO_4/Cu$. A membrane was employed to maintain separation between the metal ions while allowing the free passage of protons. The Daniell cell was not widely used since the best available separator for the cell was an animal membrane with a relatively short life. An attempt was made to substitute fragile, bulky ceramics for the animal membrane in a Daniell cell, but such ceramics were ineffective over extended periods of usage since they allowed eventual mixing of the metal ions through diffusion. The Daniell cell was also not expected to be a secondary or rechargeable battery since in its time it was the only source of electrical power.

Modern proton conductors assume the form of very thin fused glass membranes, such as used in pH sensors, or salts, such as $LiN_2H_5SO_4$, $KHF_2$, and $NH_4ClO_4$ which are not sufficiently conductive at room temperature to be useful in most electrochemical applications. In all known proton conductors, a limited amount of water is known to be present. The water either contributes to or provides an active center or medium for proton transport. Many natural or biological membranes are known to conduct protons at room temperature with fair conductivities, but in general are not suited for commercial application due to their lack of availability or poor chemical and thermal stability.

In U.S. Pat. No. 3,883,784 entitled "Electrical Device With High Dielectric Constant", assigned to the inventor of the present invention, an electrical device having a pair of conductive sheets with a layer of an organic polymeric association product sandwiched between these sheets is disclosed. The patented device functions because of limited proton displacement from bound proton donors. The dried association product preferably comprises polyethylene oxide of a high concentration, i.e., between 60 and 90% by weight of the total, and a polymeric resin preferably a phenolic compound.

U.S. Pat. Nos. 3,390,313 and 3,427,247, respectively entitled "Electromechanical Devices Using Ionic Semiconductors" and "Electroviscous Compositions", disclose a proton conductive coating on silica which operates through proton acceptor and donor sites.

Polymeric permselective membranes do not have specific ion selectivity but rather have variable permeability to specific groups of ions such as anions or cations. Further selectivity may be based upon ionic size, hydration, activity, etc. Selectivity is due to pores of limited size containing isolated charge centers within the pore walls. The charge centers may be furnished by introduction of ion exchange monomers. Some examples of permselective membrane materials are: sulfonated poly- (styrene-divinyl benzene) copolymer, perfluorinated ionomers containing sulfonate and/or carboxylate active sites, or a copolymer of acrylic acid and divinyl benzene. In these polymers, the active charge ion exchange radical appears at various intervals along the polymeric chain resulting in random isolated charges. Accordingly, the distance between the charge sites in such polymers is important since if they are too close swelling of the pores results and if they are too far distant insufficient selectivity is obtained.

Pore size is a basic problem in producing polymeric membranes and most thick film or solid processes involve use of an additive called a pore former, which may be a solvent which evaporates leaving a porous or free volume.

Hydrogels which are characterized by having a high degree of water absorption or the ability to modify water have been employed in electrolytes. Such hydrogels have the ability to modify or immobilize the electrolyte and to form a physical barrier to the migration or diffusion of materials through the structure without significantly lowering the conductivity of the electrolyte. Hydrogels have been used historically as thickeners, film forming agents or as barriers. For example, in drug delivery systems an active drug can be carried in an open immobilized structure of electrolyte and hydrogel. The rate of diffusion of the drug through the structure is controlled by the characteristics of the selected hydrogel. The porosity and hydrophilicity of hydrogels can be decreased by cross-linking the hydrogel or by copolymerizing two different hydrogels. As another example, hydrogels have been used in batteries to provide a barrier which will allow the diffusion of ions, absorb the electrolyte, provide electronic separation and keep the solid particles or constituents separate. The most widely used hydrogel materials have been starches, cellulosics, and natural gums—all of which absorb many times their own weight in water or electrolyte and form gels. These hydrogels also have a high diffusion rate which is important in most applications to single electrolyte systems.

Polymeric "nonporous" membranes are typically thin films with diffusion through the free volume offered by the amorphous phases of the physical structure of long chain polymers. Cellulose and its derivatives are examples of materials which, when in film form, exhibit such behavior. Aromatic polyamide-imides, chemically modified polysulfones, and ethylene oxide grafted "Nylon-6" are examples of noncellulosic membranes.

Permselective membranes have been used to replace anions or cations such as in the sweetening of citrus juice. Typically, a sweetening process uses two anion selective membranes separating the juice from two alkaline electrolytes. A passage of current through all three chambers causes hydroxyl anions to pass from one alkaline electrolyte into the juice to neutralize the acid hydrogen cation while the citrate anions are passed into the other alkaline electrolyte forming a salt.

Certain biological materials such as proteins are known to be semiconductors with high activation energies inversely proportional to absorbed water. These biopolymers have a relatively low ionic conduction, i.e., ionic conduction proportional to water absorption.

BRIEF SUMMARY OF THE INVENTION

This invention comprises the discovery that long polymeric chains which immobilize water, i.e., absorb and bind or modify water when dispersed in a nonporous matrix, can transport ions provided that: 1) a source of the ions exists adjacent to one side and 2) a constant removal of the same ions occurs on the other side. In the practice of this invention it is assumed that each dispersed polymer, the polymers hereinafter being referred to as hydrogels, has an associated chain of water molecules attached to its length or spine. Each water chain functions as an ionic semiconductor with a conductance which is low compared to a water channel or pore as exists in other polymeric membrane materials. As a semiconductor, materials in accordance of the invention have a high activation energy of conductance, i.e., an energy well above 5 kiloJoules/mol, which makes conductivity very dependent upon temperature. This invention additionally encompasses the discovery that it is possible to achieve a high density of conductive molecules to thereby obtain conductivity comparable to porous ion exchange membranes. A critical upper density level is found when the hydrogel molecules are dispersed within an inert matrix, this critical level being exhibited by the development of pores and gelling. If the density is too low, the conductivity of the material becomes too low for most applications since the matrix contains no water molecule chains. The invention is able to utilize a polymer such as polyvinylidene chloride which has a low free volume and has applications because of its low permeability. It should be noted that the chains of water of this invention are different from the channels of water in other membranes. The chains of water of this invention are bound to the matrix which is of itself nonporous and hence the water molecules are not free to move as they may in open channels of water as occur in porous materials. Since the water molecules in the bound chain are immobilized and thus cannot diffuse, the water chain does not function as a pore.

Briefly stated, the invention in a preferred form is an ionic semi-conductive material which has 10 to 50 percent by weight of a water absorbing and bonding long chain molecule (hereinafter called a hydrogel) dispersed within an inert and nonporous matrix. The hydrogel and matrix form a composite wherein there is sufficient bonding between the hydrogel and the matrix so that the composite is inert, there is no substantial leach out of the hydrogel, and the quantity of water that can be absorbed by the composite does not exceed the weight of the composite.

The transport of ions through the composite depends upon the simultaneous existence of an ion source upon one side and the existence of an ionic depletion gradient upon the other.

The water bonding material (hydrogel) is preferably selected from the group consisting of the synthesized or man-made long chain polymeric hydrogels including polyethylene oxide, polyacrylic acid and polyacrylamide. Hydrogels obtained from natural sources such as hydroxyethyl cellulose, gelatin, pectin, cellulose, and starch may also be utilized with a sacrifice in certain operational characteristics. The best performance is obtained with high molecular weight and electrochemical non-ionic hydrogels.

The matrix material is preferably selected from the group consisting of polyvinylidene chloride, polyvinylidene dichloride, polyvinyl chloride, polyvinylidene flouride, polyethylene, polypropylene, and polyurethane. A coupling agent may be added to the composite to facilitate the bonding between the hydrogel and the matrix. The coupling agent, if employed, is preferably selected from the group consisting of polyacrylic acid, phenolic resin, cellulosic titanate, carbon, lignin, and silica. Many commercial plastic resins or latexes are able to bond certain hydrogels without added coupling agents.

A method for making a membrane in accordance with the present invention includes dispersing a hydrogel in a polymer, i.e., an inert matrix material, which has the necessary physical bulk properties. The weight of the dispersed hydrogel will be in the range of 10 to 50 percent of the total weight of the hydrogel-matrix material. The hydrogel and matrix material are mixed to obtain a substantially uniform distribution of the hydrogel throughout the matrix. The mixture may be formed into a sheet or other required geometry. The mixing process typically comprises the steps or melt blending and pressure mixing the hydrogel and matrix material. The mixture may be dissolved or dispersed in a solvent and deposited on a substrate and dried or fused. Water based resins such as latexes can also be used with thorough mixing of the liquid resin and hydrogel. As noted above, a coupling agent may be added to the hydrogel or to the matrix material to facilitate bonding with the matrix material. Unlike conventional polymeric membranes, the free volume should be kept at a minimum.

DETAILED DESCRIPTION OF THE INVENTION

Figure 1:
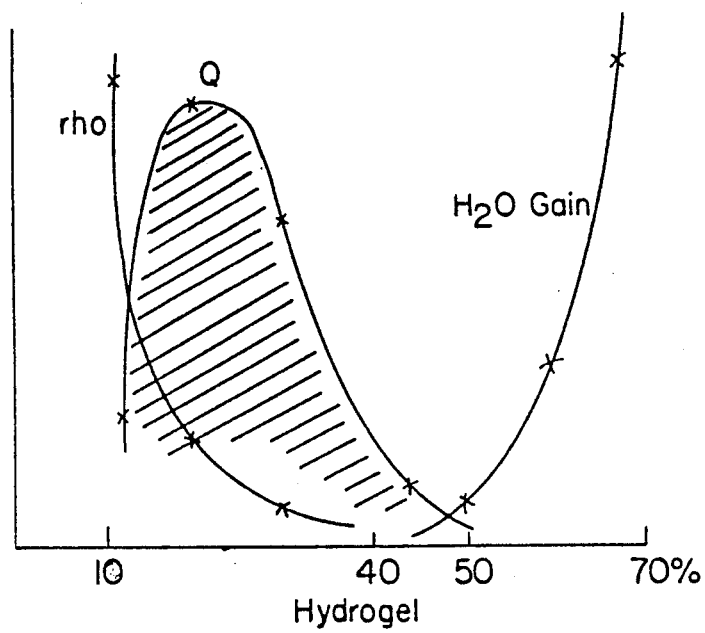
FIG. 1 is a graph illustrating resistivity, the quality factor and the water absorption gain for various concentrations in membranes of the present invention.

In accordance with the invention, a membrane or composite material which may transport certain ions, and which may exhibit preferential ion transport or water vapor transmission characteristics, results from a restricted concentration of hydrogel, i.e., water modifying polymer, dispersed and confined within an inert matrix which is not of itself porous. The composite material has 10 to 50 percent by weight of hydrogel dispersed in the matrix in such a manner that sufficient bonding is provided between the hydrogel molecules and the matrix material to prevent the hydrogel molecules from leaching out and also to provide a material composite which is inert to the environment. In some applications, physical intertwining of the matrix and hydrogel molecules may furnish sufficient bonding.

It is believed that the invention may best be described and appreciated by briefly outlining known and/or theorized properties and characteristics of a composite material comprising a hydrogel containing nonporous matrix.

In idealized form, such a composite material is theorized to consist of separate linear high molecular weight hydrogel chains which are aligned in parallel fashion extending from one surface to the other and are bound within the containing matrix. The hydrogel molecules are single chain linear polymers with a high degree of hydrophilicity. Each hydrogel chain is ideally separated (non-crystallized) with other hydrogel molecules so that excess swelling or gellation does not occur between the molecules. When the hydrogel composite is placed in an electrolyte or a water solution, the hydrogels absorb a limited amount of water with one molecule of water bonding to each active site on the hydrogel polymer.

An idealized model comprises a series of water molecules evenly spaced with such a close proximity that protons and other ions may freely pass along the spine of the hydrogel chains. (It is not yet known whether ions traverse from bound water sites to bound water sites, or from empty water sites to empty water sites or whether ions migrate via vacancies of atoms within the bound water molecules). Each molecule of water is sufficiently bound so that the water molecule is not free to move by normal diffusion, i.e., the water in the sheath essentially assumes ice-like characteristics. The hydrogel chains thus serve to provide immobilized or "frozen" sheaths of bound water molecules. The sheaths of water or the water bonding sites and thermal energy are theorized to provide the mechanism for ion conduction.

The take-up or absorption of water by hydrogels is itself theorized to involve sequential ion transfers as opposed to an inflow of freely moving water molecules as is common with pores or channels. Consequently, it may be assumed that water may permeate the composite material as separate hydroxyl and hydrogen atoms and the resulting permeation of the water throughout the hydrogel material may thus result from ions "hopping" from a filled site to an empty site along a hydrogel chain. This "hopping" phenomenon provides an explanation for the pervaporative properties of the novel hydrogel containing composite materials of the present invention. The pervaporative properties refer to the phenomena wherein, even though water will not pass through the "waterproof" composite materials, the water vapor equilibrium can be maintained by the drier side of the hydrogel material evaporating water while the wetter side of the composite material supplies replacement water ions, i.e., the materials of the present invention are "breathable".

Ion transport through hydrogel containing composite materials in accordance with the invention is theorized to proceed in a manner analogous to the take up of water by the hydrogel chains with ions "hopping" from water molecule to water molecule or from a donor site to an acceptor site in a manner analogous to the conventional proton transport theory for ice and other proton conductive materials. It is of course possible that there are active sites on the hydrogel chain which function as do the hypothesized water sites. The process of ion transport involves a transfer of energy from an acceptor site to a trapped ion. The energy for such transfers is supplied by thermal energy which is demonstrated by the high temperature coefficients or activation energies of the materials of this invention. The ion conduction process is properly characterized as a facilitated carrier process rather than the previously known solubilization and channel conduction process which occurs in conventional permselective membranes.

An unexpected property of the membranes of this invention is that ions are not transmitted through the membrane if only a concentration, pressure, or voltage gradient exists across the membrane. If fluids of different heights or ionic concentration or with a voltage gradient without a current flow exist across the membrane, no ion transport occurs because of these conditions alone as is common with commercial membranes.

If two ionic mixtures are separated by the membranes of this invention, no ion transfer (no diffusion) will take place as long as the electrolytes are each at equilibrium. Under ideal conditions, it is assumed that ions can move along the hydrogel chains and form electrical double layers at the membrane/electrolyte interfaces to balance the chemical potential. This is similar to the migration of holes and electrons in an electronic semiconductor under an external field to form a potential barrier at a junction. This potential barrier is stable with time and charges can flow through the material only if an equal number of charges are being removed from one of the interfaces to provide "holes" to which the ions may "jump". The ion transfer process is believed to require both the availability of ions on one side of the membrane and the removal of ions on the other side. The inner charge transfer of the membrane is, therefore, coupled with the external ionic electrochemical depletion gradient and therefore to the electrode reactions in an electrochemical cell. Selectivity of the membrane, i.e., the preferred ion transfer, thus appears not to be determined so much by the membrane characteristics, but by the electrode/electrolyte reactions or surface ionic concentration gradient variations.

The ion which is transferred through the membrane may not be the ion oxidized or reduced at an electrode since the ion reaction at the electrode may in turn react with or be the result of another reaction in the electrolyte which in turn causes the increase or decrease in the activity or concentration of another ion at the surface of the membrane.

Under ideal conditions, as discussed above, a single chain of water is assumed to exist along which ions can pass by "hopping" from water molecule to water molecule. It is assumed that the surrounding matrix contains no charges or can not interact in any manner with the transfer of ions. Under these ideal conditions, it can be expected that there will be a velocity difference between different ions since different energies will be required for them to "hop". Experiments demonstrate that the ions do in fact have relative velocities corresponding closely to their relative velocities at infinite dilution in water. That is, protons will be transported at about 6 times the velocity of copper ions, ($H+ = 340$ mho-cm$^2$/equivalent and $Cu++ = 55$ mho-cm$^2$/equivalent for their limiting equivalent conductance at infinite dilution). This property allows usage of the membranes of the invention in chemical separations.

An unexpected characteristic of the composite materials of the present invention, and thus of the theorized ionic conduction process, resides in the fact that the ionic conduction through the material does not require the presence of an inner electric field and the matrix can be made electrically conductive without limitation of the conduction process. This is contrary to the normal considerations for membranes. Further, the ionic conductance of the material is not highly dependent upon the thickness of the material as is normal for most conductive materials. The transfer of ions in the material is highly dependent upon thermal energy which supplies the transfer energy as well as empty receptor sites in the adjacent water molecules or acceptor sites on the chain. It is the requirement for both heat and an empty "hole" in addition to a source of ions in order for an ion to move which characterizes the operation of the materials. For holes to continuously exist, there must be a continuous removal of ions from the surface of the membrane, i.e., an ion depletion gradient must exist. This in turn requires that ions be continuously removed from the electrolyte which relates the inner transfer of ions to the reactions within the electrolytes rather than to concentration differences or pressure.

Under less than ideal conditions, i.e., when working with materials which can be practically manufactured, the molecules of the hydrogel material do not align in a perfectly parallel orientation nor are the hydrogel molecules uniformly spaced throughout the matrix. Under such real world conditions, the orientations of the hydrogel molecules tend to approach more of a "can of worms" model. At a threshold density level, if the density of the hydrogel molecules is decreased, conductive paths through the matrix theoretically decrease since single polymeric chains are no longer continuous from one side of the hydrogel material to the other side and isolated chains of hydrogel molecules are not in contact with either a surface of the hydrogel material or other chains for ion transference. With increasing density of hydrogel molecules, the adjoining of hydrogels or crystallization can take place with no separating matrix. At such crystallization sites, large channels of water may form many molecules deep or water or electrolyte may be absorbed at the sites but not be tightly bound. These latter areas of joined hydrogels without a retaining matrix may display the characteristics of a normal dissolved or gelled hydrogel with a large water absorption but without selective ion conductance. The areas of joined hydrogel molecules are believed to function as do the centers formed by grafted or added active ion centers of conventional ion exchange materials.

In accordance with the invention, the hydrogel/matrix composite may, depending upon the hydrogel density, function as a composite material having a low ionic conductance which approaches that of the matrix material (if the hydrogel content is too low) or a material with a very high water content which behaves as a gel with high diffusion (if the hydrogel concentration is too high).

The effect of encapsulating the individual hydrogel (HYD) molecules and limiting the water absorption of the hydrogel/matrix composite can be ascertained from Table 1. Table 1 illustrates a comparison of the hydrogel concentration before (dry) and after (wet) soaking the hydrogel/matrix composite in water. The hydrogel concentration is expressed as a weight percent of the total hydrogel/matrix composite material for four different hydrogel concentrations. In the examples from which the Table 1 data was collected, the hydrogel was polyethylene oxide (WSR-301 Polyox, Union Carbide Corporation) and the matrix material was a phenolic resin (12704 Phenolic resin phenol formaldehyde, Durez Division of Hooker Chemical Corporation).

TABLE 1

| | | | | |
|---|---|---|---|---|
| wgt % of HYD (dry) | 67 | 60 | 50 | 44 |
| wgt % of HYD (wet) | 2 | 6 | 33 | 36 |
| water gain (times) | 27 | 10 | 1 | 0.5 |
| H$^2$O/HYD (wet) | 40 | 17 | 2 | 1 |

As can be determined from Table 1, the ratio of the absorbed water to the initial weight increases exponentially with increasing initial percentage of hydrogel. This characteristic may be explained by the increasing numbers of associated hydrogel molecules which are capable of maintaining a channel of water between them as well as by the weakening of the restraining structure of the surrounding matrix.

Table 2 provides a comparison of membrane resistivity (rho=Ohm-cm$^2$), and the electropermeability of copper (P=micrograms per membrane voltage drop-cm$^2$-hour), versus the dry percentage weight of hydrogel in the hydrogel/matrix composite (% HYD) and the percentage gain in weight of the composite after soaking in water. In the examples from which the data of Table 2 was collected, the hydrogel material (HYD) is polyethelene oxide (WSR-301 Polyox, Union Carbide Corporation) and the matrix material is polyvinylidene chloride (864 "Saran" resin, Dow Chemical Corporation). The test cell was a Pt/H$_2$SO$_4$/CuSO$_4$/Cu couple driven with a constant current operated for two hours with the copper electrode negative. The expected reactions can be written as:

cathode: Cu° + H$_2$SO$_4$ − 2e$^-$ − 2H + CuSO$_4$

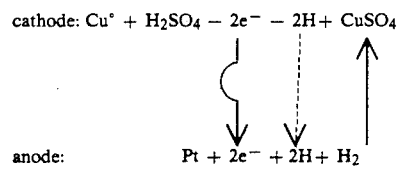

anode: Pt + 2e$^-$ + 2H + H$_2$ where the electrochemically formed protons are transferred through the membrane as indicated by the dashed line and the electrons are transferred by the external circuit indicated by a solid line. A second reaction can also take place, which is the normal copper plating equation:

anode: Cu° − 2e$^-$ ⟶ Cu++

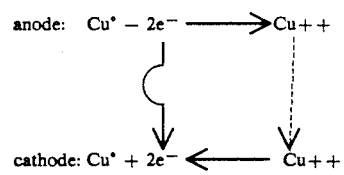

cathode: Cu° + 2e$^-$ ⟵ Cu++ where the Cu++ ion is transferred through the membrane and plates on the cathode. This reaction competes with the first reaction and is reduced by complexing of copper ions in the anolyte and an increase in the H$_2$SO$_4$/CuSO$_4$ ratio. If a membrane obtains equilibrium water uptake and is then suddenly used as a membrane in the above cell, a time factor becomes manifest, since it takes time for the copper ions to traverse the already saturated water chains. The time for an equilibrium output of copper/proton ion ratio in the catholyte will depend upon the current density, the thickness of the membrane and the number of hops along the chain. Any increase in the amount of copper over 16% of the total current after equilibrium and with low copper complexing has been found to be indicative of pore or channel formation. The resistivity, however, will depend upon the number of chains. Membranes can be evaluated therefore by comparing resistivity and the electropermeation of copper at constant current over a fixed time interval. Low copper transfer and low resistivity are indicative of better membranes according to this invention.

TABLE 2

| % HYD | % GAIN ($H_2O$) | rho | P | Q |
|---|---|---|---|---|
| 12 | 11 | 131 | 51 | 150 |
| 20 | 24 | 35 | 6 | 5100 |
| 30 | 47 | 9.6 | 280 | 370 |
| 40 | 87 | 0.3 | 60,000 | 60 |

As can be determined from Table 2, the resistivity is an inverse exponential function of the percentage of hydrogel as expected. The electropermeation of copper increases with the increasing percentage of the hydrogel presumably because of the increasing numbers of associated hydrogel molecules which can form gelled water channels. The decreases in the electropermeation from the 12 percent concentration to the 20 percent concentration can be explained by the rapid decrease in resistivity and hence the decrease in the membrane voltage drop as the hydrogel content decreases.

FIG. 1 is a composite graphical representation of the data of Table 1 and Table 2. Curve 10 illustrates the resistivity data of Table 2. Curve 20 illustrates the water gain data of Table 1. The curve 30 is a smoothed curve representing the quality factor data of Table 2. The criticality of the Q curve is quite evident. It should also be appreciated from FIG. 1 that the percentage of hydrogel used for a given application is dependent upon the compromising of the actual operating characteristics which are desired. For instance, if low diffusion is of prime importance, then the percentage of hydrogel used will be lower than if a low resistivity is of prime importance. The actual measured characteristics as set forth in Tables 1 and 2 depend upon the specific hydrogel. Some hydrogel materials and the associated water will naturally be better conductors of the ion of interest than others because of better site to site spacing along the chains.

FIG. 1 is, however, generally exemplary of graphical representations of the properties of hydrogel materials in an inert resin matrix in accordance with the present invention. Curves derived for other combinations of hydrogels and matrices can be expected to deviate only slightly with respect to abscissa coordinates and quite strongly with respect to the ordinate coordinates.

Membranes in accordance with the present invention are formed from two basic components, the hydrogel and the matrix. The hydrogel material must be dispersible throughout the matrix. Sufficient bonding between the hydrogel and the matrix is required to prevent leaching of the hydrogel. The matrix must also exhibit mechanical properties sufficient for the end usage. Conductive particles, such as carbon or metal powder, or fibers can be added to the hydrogel material to reduce the inner electrical field or to provide electron conductance through the material. Electrochemically active and other materials may also be added to the composite. For instance, special polymeric electrodes can be formed by combining an active electrode material such as zinc, silver oxide, $M_nO_2$, or lead with the composite containing an electron conductive material. Such electrodes operate by conducting the exchange electrons through the electron conduction portion of the composite and the exchange ions through the water chains.

The composite materials of the invention may be prepared by using either a dry mix or a liquid mix. The liquid mixes are used primarily in the application of a coating to a substrate or in the fabrication of very thin membranes. The dry mixes are prepared by state of the art techniques for the production of polymeric alloys. The principal problem which is ordinarily encountered in alloying polymers is the obtaining of sufficient bonding between the two materials. The mixing rate, shear forces, temperature and time are all factors in obtaining positive bonding characteristics. Coupling agents can be added to facilitate the bonding and many commercial suppliers of resins add coupling agents, plasticizers, anti-oxidants, etc., which may serve to assist in the binding of hydrogels. Materials such as silica and carbon have been successfully employed as coupling agents. Another technique employed to facilitate the bonding is to first associate two hydrogels together or to insolubilize a hydrogel to produce a less active hydrogel molecule but one which has better bonding characteristics with the matrix material.

The ratio of hydrogel to the matrix may be varied to yield materials having a wide range of properties. In general, composites having a low ratio of hydrogel to matrix material result in a low ionic permeation with near zero diffusion, low swelling (water absorption), limited surface activity and very favorable mechanical characteristics of the composite. In the case of composites having a high hydrogel material to matrix material ratio, high swelling (water absorption), high surface activity, high ionic conductivity, increased diffusion due to channel formation and unique physical characteristics are obtained. The materials forming the composite membranes may be compounded by state-of-the-art techniques including dry or melt blending or solvent dispersion and mixing. Normal precautions must be taken to prevent over or under mixing which results in either excessive molecular weight reduction through chain breakage or in low dispersion and poor association. Care must also be taken with time-temperature cycles to avoid excessive oxidation or thermal degradation.

For Examples 1-8 and 12-19, below, sheets or solid thick films of the hydrogel materials were prepared by weighing and mixing the dry ingredients and then blending the ingredients in a two roll chemical mill or in a heated press. The mixing in the mill was in accordance with normal usage. A laboratory press was found satisfactory for preparing small sample lots. The mixed, weighed samples were melt blended between two flat plates using conventional mold release agents to prevent adhesion. The temperature was adjusted to compromise the thermal degradation with the viscosity and ease of mixing as common to the art. Pressure was applied to force the shearing flow of the melt between the plates and, hence, the mixing of the matrix and hydrogel materials. The press and the plates were then opened and the pressed sheet was folded or formed into a compact mass and then repressed. This latter procedure was continued until the materials were uniformly mixed. The final pressing yielded flat sheets which were then cut to size for testing purposes. The thickness of the sheets of composite was typically between 0.02 and 0.03 cm (in thickness). Other methods of mixing such as extrusion, heat blending and pelletizing may also be used to form the composite material.

For Examples 9–12, below, liquid mixes were prepared by state-of-the-art techniques. The hydrogels were usually first dispersed in an organic solvent in which the hydrogel is not soluble. The matrix and additives for further mixing were added to the hydrogel and solvent. Water was then slowly added during the mixing process. The viscosity and flow characteristics of the resulting solution were controlled to some degree by the amounts of the solvent and the added water. Once the mixing was complete, the mixture was applied to a substrate or cast into films by known methods. The film or coating was then allowed to dry and was baked or cured depending upon recommendations from the manufacturers of the ingredients. In general, lower temperatures and longer times of baking or curing are preferred instead of short times at high temperatures.

The membranes of the present invention differ from previous hydrogel material composites in the dispersion of critical quantities of hydrogel in the final water swollen state in an inert and nonporous matrix. The dispersion of *separated* hydrogel molecules minimizes crystallization or hydrogel to hydrogel association and hence decreases channel formation and water absorption. The present invention avoids the formation of a gel or intercoupling of hydrogel molecules whereas past usage desired the gelation of hydrogels.

An inert matrix functions to *separate* and restrain the hydrogel molecules, and consequently, there is substantially less swelling or weight gain due to the absorption of water by the formed material. In accordance with the invention, the proportion of hydrogels employed is in the range of between 10 and approximately 50 percent by weight of the dry composite. The proportion may be further limited for melt-mix and solvent based systems which require a ration from about 20 to 50% and for water based systems which require about a 10 to 40 percent ratio of hydrogel to matrix. This results in a composite material which does not absorb sufficient water to double the weight of a formed membrane. General limitations may also be placed upon the selected hydrogels or water modifiers used as constituents in the membrane. A first limitation is the compatibility of the hydrogel with a given matrix material. A second limitation is the stability of the hydrogel both mechanically and chemically at the temperature of operation for the membrane. A third limitation is the conductivity of the hydrogel/water, particularly when ion transfer is of primary importance. A fourth limitation is that the hydrogel must have sufficient molecular weight or be of such a length that the number of hydrogel molecules necessary to connect one side of a membrane to the other are minimized.

The following examples are given for purposes of illustration only in order that the invention may be more fully understood. The examples are not intended to in any manner limit the practice or scope of the invention. Unless otherwise specified, all (specified) proportions are given by weight.

EXAMPLE 1

A sheet of material was prepared from 12 percent Union Carbide Corporation 4,000,000 molecular weight polyethylene oxide sold under the trade name "Polyox 301" and 88 percent Dow Chemical Corporation polyvinylidene chloride sold under the trade name "Saran 864 resin". The mixture was heat blended and pressure mixed in a press as previously described to form flat sheets of material. The formed sheets were weighed and then soaked in water at room temperature for at least two hours. The sheets were blotted dry and reweighed. The absorbed water was found to increase the weight of the sheets by 11 percent.

EXAMPLE 2

A sheet of material was prepared from 20 percent Union Carbide Corporation 4,000,000 molecular weight polyethylene oxide sold under the trade name "Polyox 301" and 80 percent Dow Chemical Corporation polyvinylidene chloride sold under the trade name "Saran 864 resin". The foregoing materials were mixed, heat blended and pressure mixed in a press as previously described to form flat sheets of material. The formed sheets were weighed and soaked in water at room temperature for at least two hours. The sheets were blotted dry and reweighed. The absorbed water was found to increase the weight of the sheets by 24 percent.

EXAMPLE 3

A sheet of material was prepared from 15 percent B. F. Goodrich Co. 3,000,000 molecular weight polyacrylic acid sold under the trade name "Carbopol 934", 15 percent Union Carbide Corp. 4,000,000 molecular weight polyethylene oxide sold under the trade name "Polyox 301", and 70 percent Kay-Fries, Inc. polyvinylidene fluoride sold under the trade name "Dyflor 2000". The polyacrylic acid was mixed with the polyethylene oxide to insolubilize the polyethylene oxide and to facilitate bonding to the polyvinylidene fluoride matrix. The polyacrylic acid is also a hydrogel. The foregoing materials were mixed, melt blended, and pressure mixed in a press as previously described to form flat sheets of material. The sheets were weighed and then soaked in water at room temperature for at least two hours. The sheets were blotted dry and reweighed. The absorbed water was found to increase the weight of the sheets by 16 percent.

EXAMPLE 4

A sheet of material was prepared from 20 percent B.F. Goodrich Co. 3,000,000 molecular weight polyacrylic acid sold under the trade name "Carbopol 934", 20 percent Union Carbide Corporation 4,000,000 molecular weight polyethylene oxide sold under the trade name "Polyox 301", and 60 percent Kay-Fries, Inc. polyvinylidene flouride sold under the trade name "Dyflor 2000". The polyacrylic acid was mixed with the polyethylene oxide to insolubilize the polyethylene oxide and to facilitate bonding to the polyvinylidene fluoride matrix. The polyacrylic acid is also a hydrogel. The foregoing materials were mixed, melt blended, and pressure mixed in a press as previously described to form flat sheets of material. The sheets were weighed and then soaked in water at room temperature for at least two hours. The sheets were blotted dry and reweighed. The absorbed water was found to increase the weight of the sheets by 33 percent.

EXAMPLE 5

A sheet of material was prepared from 25 percent B. F. Goodrich Company 3,000,000 molecular weight polyacrylic acid sold under the trade name "Carbopol 934", 20 percent Union Carbide Corporation 4,000,000 molecular weight polyethylene oxide sold under the trade name "Polyox 301", and 55 percent Kay-Fries, Inc. polyvinylidene fluoride sold under the name "Dyflor 2000". The polyacrylic acid was mixed with the polyethylene oxide to insolubilize the polyethylene oxide and to facilitate bonding to the polyvinylidene fluoride matrix. The polyacrylic acid is also a hydrogel. The foregoing materials were mixed, melt blended, and pressure mixed in a press as previously described to form flat sheets of material. The sheets were weighed and then soaked in water at room temperature for at least two hours. The sheets were blotted dry and reweighed. The absorbed water was found to increase the weight of the sheets by 42 percent.

EXAMPLE 6

A sheet of material was prepared from 50 percent B.F. Goodrich Corporation 3,000,000 molecular weight polyacrylic acid sold under the trade name "Carbopol 934" and 50 percent Borden Company homopolymer polyvinyl chloride resin sold under the trade name VC-54". 0.025% neoalkoxy titanate sold by Kenrich Petrochemicals, Inc. under the designation "LICA 12" was added to facilitate the bonding of the hydrogel to the matrix. The foregoing materials were mixed, melt blended, and pressure mixed in a press as previously described to form flat sheets of material. The sheets were weighed and then soaked in water for at least two hours. The sheets were blotted dry and reweighed. The absorbed water was found to increase the weight of the sheets by 76 percent.

EXAMPLE 7

A sheet of material was prepared from 25 percent Union Carbide Corporation hydroxyethyl cellulose sold under the trade name "Cellosize QP 4400 H", 25 percent polymerizable cellulosic sold under the designation "105" by A.E. Staley Manufacturing Company, and 50 percent Borden Company homopolymer polyvinyl chloride resin sold under the trade name "VC-54". The cellulosic was added to facilitate the bonding of the hydrogel to the matrix. The cellulosic may also partially function as a hydrogel. The foregiong materials were mixed, melt blended, and pressure mixed as previously described to form flat sheets of material. The sheets were weighed and then soaked in water at room temperature for at least two hours. The sheets were blotted dry and reweighed. The absorbed water was found to increase the weight of the sheets by 41 percent.

EXAMPLE 8

A sheet of material was prepared from 40 percent pectin, 10 percent polymerizable cellulosic sold under the designation "106" sold by A.E. Staley Manufacturing Company, and 50 percent Borden Company homopolymer polyvinyl chloride resin sold under the trade name "VC-54". The cellulosic was added to facilitate the bonding of the hydrogel to the matrix. The cellulosic may also partially function as a hydrogel. The foregoing materials were mixed, melt blended, and pressure mixed as previously described to form flat sheets of material. The sheets were weighed and then soaked in water at room temperature for at least two hours. The sheets were blotted dry and reweighed. The absorbed water was found to increase the weight of the sheets by 13 percent.

EXAMPLE 9

A coating was prepared from 20 percent Union Carbide Corp. 4,000,000 molecular weight polyethylene oxide sold under the trade name "Polyox 301" and 80 percent Durez phenol formaldehyde sold under the trade name "12704 Phenolic resin". The foregoing materials were mixed and water was added to the mixture during the mixing process. The coating was applied to a commercial grade of Kraft paper. The coating was allowed to dry and was treated as previously described.

EXAMPLE 10

A first coating was prepared from 33 percent Union Carbide Corp. hydroxyethyl cellulose sold under the trade name "Cellosize QP 4400 H" and 67 percent Durez phenol formaldehyde sold under the trade name "12704 Phenolic resin". The foregoing were mixed and water was added to the mixture during the mixing process. A second coating was prepared from 33 percent B.F. Goodrich Co. 3,000,000 molecular 934" and 67 percent Durez phenol formaldehyde sold under the trade name "12704 Phenolic resin". The foregoing materials were mixed and water was added to the mixture during the mixing process. The first coating was applied to one side of a commercial grade of Kraft paper and the second coating was applied to the other side of the Kraft paper. The coatings were allowed to dry and were cured as previously described.

EXAMPLE 11

A coating was prepared from 9.7 percent Union Carbide Corp. 4,000,000 molecular weight polyethylene oxide sold under the trade name "Polyox 301", 58.3 percent Dow Chemical Corp. copolymer of vinylidene chloride and others sold under the trade name "RAP 184 Latex", and 2 percent B.F. Goodrich Co. 3,000,000 molecular weight polyacrylic acid sold under the trade name "Carbopol 934". The polyacrylic acid was added to the polyvinylidene chloride to insolubilize the polyethylene oxide and facilitate the bonding. The foregoing materials were mixed and water was added to the mixture during the mixing process. The coating was applied to a commercial grade of Kraft paper. The coating was allowed to dry and was baked as previously described.

EXAMPLE 12

A coating was prepared from 20 percent Union Carbide Corp. hydroxyethyl cellulose sold under the trade name "Cellosize QP 4400 H" and 80 percent Loctite Corp. two part expoxy sold under the trade name "EPOXE". The foregoing materials were mixed and water was added to the mixture during the mixing process. The coating was applied to a commercial grade of Kraft paper. The coating was allowed to dry and to cure.

EXAMPLE 13

A sheet of material was prepared from 30.8 percent Union Carbide Corp. 4,000,000 molecular weight polyethylene oxide sold under the trade name "Polyox 301", 56.8 percent polypropylene resin sold under the trade name "Pro-fax PC072" by Himont U.S.A., Inc., 10 percent Cabot Corporation fumed silica sold under the trade name "Cab-O-Sil EH-5", and 12.4 percent phenol formaldehyde sold under the trade name "Durez 12704 Phenolic resin" by Hooker Chemical Corporation. The poly-propylene resin and silica were premixed to facilitate bonding with the polyethylene oxide and phenolic. After pre-mixing, the foregoing materials were mixed, melt blended, and pressure mixed as previously described to form flat sheets of material. The sheets were weighed and then soaked in water at room temperature for at least two hours. The sheets were blotted dry and reweighed. The absorbed water was found to increase the weight of the sheets by 50 percent.

EXAMPLE 14

A sheet of material was prepared from 50 percent Allied Chemical Corporation polyacrylamide flocculent sold under the trade name "A210" and 50 percent polypropylene resin sold under the trade name "Pro-fax PC072" by Himont U.S.A., Inc. The foregoing materials were mixed, melt blended, and pressure mixed as previously described to form flat sheets of material. The sheets were weighed and then soaked in water at room temperature for at least two hours. The sheets were blotted dry and reweighed. The absorbed water was found to increase the weight of the sheets by 38 percent.

EXAMPLE 15

A sheet of material was prepared from 30 percent starch derivative sold under the tradename "SGP 147" by Henkel Corporation, and 70 percent Borden Company homopolymer polyvinyl chloride resin sold under the trade name "VC-54". The foregoing materials were mixed, melt blended, and pressure mixed as previously described to form flat sheets of material. The sheets were weighed and then soaked in water at room temperature for at least two hours. The sheets were blotted dry and reweighed. The absorbed water was found to increase the weight of the sheets by 11 percent.

EXAMPLE 16

A formulation was prepared from 33% cellulose fibers prepared from Kraft paper by soaking the paper in a heated sodium hydroxide solution, then washing, filtering and drying. The fibers contain natural hydrogel chains extending along their lengths. The fibers were dispersed in a polyvinylidene fluoride resin sold as "Floraflon 1000 LD" by Ugine Kuhlman of America, Inc. The foregoing materials were melt-mixed and extruded to form flat sheets of material. The sheets had a high resistivity of 600 Ohm-cm$^2$.

EXAMPLE 17

A two-stage formulation was prepared from 50% silica as Cab-O-Sil* (Cabot Corp. M-5 dispersed in cellosolve), 50% Gelatin USP (Knox Gelatine, Inc.) dissolved in water. The foregoing materials were mixed in a blender, spread out on a surface, and dried. Fifty percent (50%) of the foregoing dried mixture was combined with 50% polyvinylidene fluoride as Florafon* 1000 LD (Ugine Kuhlman of America, Inc.). The materials were melted, mixed and extruded to form a flat sheet of about 0.1 cm thickness with an activation energy of conduction over 10 kiloJoules/mol.

EXAMPLE 18

A sheet of material was prepared from 70 percent of a commercial polyethylene electrically conductive resin containing about 20 percent activated carbon supplied by Modern Dispersions, Inc. sold under the label of "PM 530"; 25 percent Union Carbide Corporation 4,000,000 molecular weight of polyethylene oxide sold under the trade name "Polyox 301"; and 5 percent of a modified ethylene vinyl alcohol adhesive supplied by Chemplex Company sold under the trade name of "Plexar 100". The "Plexar 100" was added to facilitate alloying the mixture. The materials were melt blended and pressure mixed as previously described to form flat sheets of material. The sheets were weighed and then soaked in water for at least two hours. The sheets were blotted dry and reweighed. The absorbed water was found to increase the weight of the sheets by 27 percent.

EXAMPLE 19

A sheet of material was prepared from a melt blend of 20 percent Union Carbide Corporation 4,000,000 molecular weight polyethylene oxide sold under the trade name "Polyox 301"; 20 percent activated carbon powder sold under the trade name "Vulcan XC 72R" by Cabot; and 60 percent polypropylene resin sold under the trade name "Pro-Fax PC072". The melt pressed sheets were soaked in water for at least two hours. The absorbed water was found to increase the weight of the sheets by 12.2 percent.

Various measurements and properties of the membranes, i.e., the sheets and coated materials, of Examples 1 through 19 are summarized and set forth in TABLE 3 below. Example R is a commercially available permselective membrane composed of perfluorosulfonic acid which is sold by DuPont under the trade name "Nafion 125". Example R is a reference material included for purposes of comparison.

TABLE 3

| Example | % Hydrogel | % H$^2$O | Rho | P | Q |
|---|---|---|---|---|---|
| 1 | 12 | 11 | 130 | 50 | 150 |
| 2 | 20 | 24 | 35 | 6 | 4800 |
| 3 | 15 | 16 | 67 | 187 | 67 |
| 4 | 20 | 33 | 26 | 40 | 1040 |
| 5 | 25 | 42 | 11 | 30 | 2900 |
| 6 | 50 | 76 | 190 | 81 | 65 |
| 7 | 25 | 41 | 40 | 625 | 40 |
| 8 | 40 | 13 | 78 | 156 | 80 |
| 9 | 20 | | 190 | 76 | 69 |
| 10 | 33 | | 170 | 17 | 340 |
| 11 | 10 | | 160 | 196 | 31 |
| 12 | 20 | | 64 | 190 | 79 |
| 13 | 31 | 50 | 50 | 450 | 44 |
| 14 | 50 | 38 | 92 | 33 | 326 |
| 15 | 30 | 11 | 200 | 340 | 15 |
| 16 | 33 | | 600 | 235 | 7 |
| 17 | 25 | | 2000 | 20 | 25 |
| 18* | 25 | 27 | 0 | NA | NA |
| 19** | 20 | 12 | 0 | NA | NA |
| R | | 9 | 1 | 86000 | 19 |

*Example 18 was constructed of an electron conducting membrane and hence the measured voltage drop across the membrane was zero. The amount of copper which permeated the membrane equalled an equivalence to less than 2.7 percent of the total current.

**Example 19 was electron conducting and had a copper permeation less than a 1.5 percent equivalence to the current with a small amount of copper plating found at the interface of air, copper electrolyte and membrane continuing a few millimeters on the membrane air interface.

The water absorption measurements (% H$_2$O) of Table 3 are a sensitive test of the materials due to the strong affinity of the hydrogels for water. Prepared samples were weighed and placed in water at room temperature and allowed to soak for at least four hours. The samples were then blotted dry and reweighed. The gain in the weight was divided by the original dry weight and multiplied by 100 to yield the percentage of water absorption gain.

The resistivity values (Rho) for Table 3 were first obtained by soaking the membrane in water to fully absorb the water and then placing the membrane in an electrochemical cell separating two electrolytes. A known current was passed through the cell and membrane, and the voltage drop across the membrane was measured with a small platinum probe after initial polarization was reached. The resistance of the membrane was obtained by determining the ratio of the voltage drop to the magnitude of the electric current. The resistivity (Ohm-cm$^2$) was obtained by multiplying the resistance by the area of the membrane exposed to the current flow. The resistivity values were determined at room temperature. Equilibrium direct current measurements were employed. The resistance values so obtained are not absolute since an emf exists across the membrane proportional to the difference in chemical potential existing between the two electrolytes. In most tests this potential increases with time because of the potential in pH which take place with a current flow.

The electrical permeation (P) for Table 3 is indicative of the passage of copper ion through the membranes under the electrochemical ionic gradient. A high percentage of permeation indicates the formation of pores or open channels of water. The membrane to be tested was placed in an electrochemical cell separating an acid copper plating solution (20% wgt $CuSO_4$, 6% $H_2SO_4$) as the anolyte and a 10% $H_2SO_4$ solution as the catholyte. A copper anode was used with a weighed platinum cathode. A known current With a density of about 6 mA/cm$^2$ was passed through the membrane for two hours. The copper ions which permeated through the membrane were plated out on the platinum cathode. The platinum cathode was weighed to determine the quantity of plated copper. During the test, the voltage drop across the membrane was measured with a platinum probe. The final electropermeation co-efficient was obtained by dividing the weight in micrograms of the copper plated on the cathode by the product of the membrane voltage drop, the effective area of the membrane and the time of the application of the electric field. The resulting electropermeation P is expressed in micrograms per (volt cm$^2$-hour).

The measured permeation values may be slightly higher than the actual values because of surface conductance over the outer edges of the membrane in addition to the transfer through the membrane. This is significant because of the high surface conductivity of the materials. The measured values may also be slightly lowered due to the observable loss of salts through piezodialysis, such salts appearing on the outer edges of the membrane and outside the cell.

The quality factor (Q) of Table 3 was determined by two operational factors, e.g., the ease of permeation of the desired ions and the rejection of the undesired ions. The quality factor Q is defined as $10^6/(\text{rho} \times P)$ where rho is the resistivity and P is the electropermeability as defined above.

The membranes of Examples 1 through 19 may find applications in many fields including hydrogen and chlorine generation, batteries, pervaporative films and materials for moisture control, biological applications, pH control, separations, metrology, fuel cells, electrochemical synthesis, and water purification.

The coated paper membrane of Example 11 above was taped to the opening of a 125 ml flask half filled with water kept at 100 degrees F. and its weight compared over time with a similar filled flask at 100° F. with no cover over the opening. The membrane covered flask demonstrated half the loss of water per hour as did the open flask indicating that the membrane had an equivalent aperture of one half the uncovered flask or functioned as if it were 50% porous. This experiment demonstrated the pervaporative properties of the membranes of this invention, in that the flask covered with the membrane could be inverted without any water leaking through the membrane (waterproof) and yet would pass water vapor to the drier external air (45% relative humidity) at a rate equal to one half that of an open flask (breathable).

As noted above, a very early Daniell cell used animal bladders or ceramics to keep zinc and copper ions separate. The cell may be designated as follows: $Zn/ZnSO_4//CuSO_4/Cu$, where the // designates a membrane without diffusion. As the cell discharges, the zinc reacts with the acid and the copper sulfate reacts as set forth below:

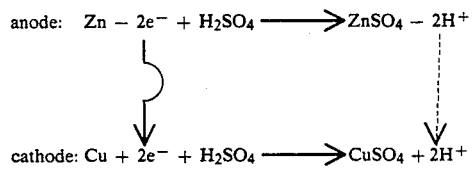

$$\text{anode: } Zn - 2e^- + H_2SO_4 \longrightarrow ZnSO_4 - 2H^+$$
$$\text{cathode: } Cu + 2e^- + H_2SO_4 \longrightarrow CuSO_4 + 2H^+$$

The anode reactions proceed to the right with the electrons flowing through the external circuit and the protons flowing through the membrane. The cathode reaction proceeds to the left with copper being deposited upon the cathode. Upon charging the cell the process is reversed, the copper dissolves, the proton flow is reversed and the zinc plates onto the zinc electrode.

The lack of commercial utility of the early Daniell cell resulted from deficiencies in the membrane. The animal membranes which were employed had a relatively short life in the caustic solutions and the alternative ceramic membranes were bulky, fragile and unable to keep the two electrolytes from mixing over prolonged periods of time. Copper and zinc would still be the choice for battery materials today since the metals are both relatively light with a high electrical charge with a theoretical capacity six times the capacity per pound of lead acid and Ni/Cad batteries. Further, both metals are in abundance, inexpensive, relatively non-toxic and non-hazardous.

Copper and zinc have problems, however, which have precluded their usage in rechargeable batteries. Zinc when used as an anode fails to replate or reform to its original shape when recharged and tends to grow very thin conductive whiskers or dendrites which can short out the electrodes in just a few recharge cycles. Copper is sufficiently soluble and mobile in most electrolytes to poison the other electrode and electrolyte, gradually dropping the battery performance. Zinc is used in short lived high energy per pound batteries with sacrificial wrapping around the zinc to prevent the formation of dendrites. Copper is not used at present in any commercial batteries.

EXAMPLE 20

To demonstrate the present invention, a Daniell cell was assembled which employed a strip of copper in an acid copper sulfate plating catholyte and a strip of zinc in an ammonium/zinc chloride anolyte. The electrolytes were separated by a membrane constructed of 6% silica, 25% Union Carbide Corporation 4,000,000 molecular weight polyethylene oxide sold under the trade name "Polyox 301", 57% polypropylene resin sold under the trade name "Pro-fax PC072" by Himont U.S.A., Inc., 12 percent phenol formaldehyde sold under the trade name "Durez 12704 Phenolic resin" by Hooker Chemical Corporation. The cell delivered an open circuit voltage of slightly over one volt with an internal resistance of about 40 Ohm-cm$^2$ at a current density of about 0.01 Amperes/cm$^2$.

EXAMPLE 21

A further Daniell cell was constructed by exchanging the anolyte of the above example with a 1N KOH electrolyte. The cell open circuit voltage rose to over 1.3 volts and the internal resistance decreased to about 16 Ohm cm$^2$ at about 0.015 Amperes/cm$^2$.

EXAMPLE 22

A further modification of the Daniell cell was tested using copper oxide as the catholyte in a mixture of silica and carbon. Equal volumes of micronized amorphous silica sold as IMSIL* A-10 by Illinois Minerals Company and commercial red copper oxide powder were mixed and placed on the catholyte compartment and moistened with 1N $H_2SO_4$. A membrane constructed from 16% Union Carbide Corporation 4,000,000 molecular Weight polyethylene oxide sold under the trade name "Polyox 301"; 8 percent activated carbon powder sold under the trade name "Vulcan XC 72R" by Cabot; 10 percent ¼ inch unsized carbon fibers sold as Fortafil* 3 supplied by Great Lakes Carbon Corporation; and 66 percent Dow Chemical Corporation polyvinylidene chloride sold under the trade name "Saran 864 resin" separated the catholyte from the above zinc/anolyte. The cell had an open circuit voltage of about 1.3 volts with an internal resistance of about 20 Ohms cm$^2$ when run at about 0.015 Amperes/cm$^2$.

Each of the above zinc/copper cells was rechargeable, limited by the morphology of the zinc which deteriorated during each recharging cycle.

EXAMPLE 23

The life of the zinc electrode of the above described cells may be extended without decreasing the performance of the cell by encapsulating zinc metal in the ionic conducting composite material of this invention made electronically conductive by adding carbon or metal particles. For example, a composite zinc electrode was constructed of 9% acrylic acid of molecular weight of about 4,000,000 (Carbopol 940, a product of B.F. Goodrich Company); 2.5% carbon powder (Vulcan XC-72, manufactured by Cabot Corporation); 4.5% unsized ¼ inch carbon fibers (Fortafil 3, supplied by Great Lakes Carbon Corporation), 5.3% polypropylene (Pro-fax PC072, manufactured by Himont U.S.A., Inc.) and 66% zinc oxide powder. The polyacrylic acid was first dissolved in water, the carbon powder added and the mixture mixed then blended in a high speed blender. The water was removed from the mixture by filtering and drying. The carbon fibers and polypropylene were added and the material melt blended. Finally, the zinc oxide was added and melt blended with the other previously mixed constituents. The resulting mixture was formed into a sheet of about 0.1 cm thickness and cut to form two pieces about 2 cm×2 cm. The two pieces were then placed on either side of a copper plated stainless steel screen and hot pressed into a one piece component. The zinc oxide was then reduced by standard electrochemical methods to form the free zinc. The $O^{--}$, $OH^-$ and $H^+$ ions are readily transported through the electrode as are the electrons to complete the electrochemical reactions.

The above described Daniell cells were rerun with the novel zinc encapsulated electrode and repeatedly charged and discharged with no evidence of deterioration of the zinc electrodes other than minor surface roughening over weeks of testing.

Similarly, other metals and materials can be encapsulated by, for example, first compounding 27% acrylic acid of molecular weight of about 4,000,000 (Carbopol) 940, a product of B.F. Goodrich Company); 7% carbon powder (Vulcan XC-72, manufactured by Cabot Corporation); 13% unsized ¼ inch carbon fibers (Fortafil 3, supplied by Great Lakes Carbon Corporation), 53% polyproplyene (Pro-fax PC072, manufactured by Himont U.S.A., Inc.) by melt blending as described above. The material to be encapsulated is then added in a ratio of about 1 to 1.5 of the above mix to the added material. An electrode with encapsulated silver oxide was found to operate with about the same current density as commercial sintered silver oxide electrodes. An electrode encapsulating lead powder was found to have equal or greater utilization when compared to commercial electrodes.

The results of zinc/copper batteries are given in the following table which lists the open circuit voltage, measured cell resistivity and calculated maximum power output for the different pH combinations of the electrolytes.

| Electrodes | | V oc | Ri | Power |
|---|---|---|---|---|
| Zn anode | Cu cathode | Volts | Ohm-cm$^2$ | mWatts/cm$^2$ |
| acid | acid | 1.1 | 40 | 8 |
| acid | base | 1.1 | 80 | 4 |
| base | acid | 1.3 | 20 | 21 |
| base | base | 1.3 | 65 | 7 |

The membranes employed in the acid-acid and base-acid cells were the same as described above for Example 20 while the membranes for the other two were 16% Union Carbide Corporation 4,000,000 molecular weight polyethylene oxide sold under the trade name "Polyox 301"; 8 percent activated carbon powder sold under the trade name "Vulcan XC 72R" by Cabot; 10 percent ¼ inch unsized carbon fibers sold as Fortafil* 3 supplied by Great Lakes Carbon Corporation; and 66 percent Dow Chemical Corporation polyvinylidene chloride sold under the trade name "Saran 864 resin".

The high conductance obtainable from the high content hydrogel membranes of this invention and the negligible diffusion make these membranes highly desirable for battery separators. The lack of diffusion keeps electrolytes from mixing and hence contributes toward an extended shelf life of a battery.

Another advantage of the use of membranes of this invention is that an optimum electrolyte can be used with each electrode and hence increased cell voltage can be obtained. It should also be noted that since the power output of a cell is proportional to the square of voltage ($P = V^2/R$), a small increase in cell voltage can yield a very significant increase in power or energy per cell. For example, in a zinc/manganese battery where the zinc half cell is alkaline and the manganese dioxide is acid, the employment of a membrane in accordance with the examples of this invention will result in a battery voltage which approaches 2.05 volts (Zn/$^-$OH=1.25 volts and H$^+$/MnO$_2$=0.80 volts). The latter represents a 37% increase in voltage and an 85% increase in power over the conventional "drycell" battery. Experimental cells employing the electrochemical selective membranes of the present invention have demonstrated current carrying capability equal to that of standard construction and were also rechargeable.

EXAMPLE 24

An example of an application of the present invention is a high voltage rechargeable battery. The battery used a membrane constructed of 37% acrylic acid of molecular weight of about 4,000,000 (Carbopol 940, a product of B.F. Goodrich Company); 10% carbon powder (Vulcan XC-72, manufactured by Cabot Corporation); 53% polypropylene (Pro-fax PC072, manufactured by Himont U.S.A., Inc.) by melt blending as described above. One half of the cell is a standard alkaline cell with a zinc anode and the other half is a standard acid cell with a lead oxide cathode. A Zn/6N KOH//6N H$_2$SO$_4$/PbO$_2$ battery was constructed and tested. The test battery had an open circuit voltage of about 2.9 volts. This open circuit voltage compares with a lithium battery. The current density of the battery was comparable to that of a standard alkaline zinc battery. The chief reactions can be simply diagrammed as follows:

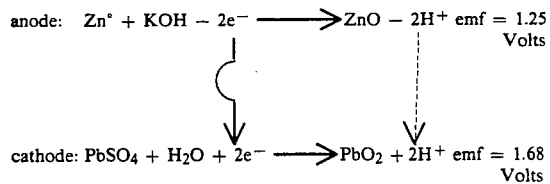

anode: Zn° + KOH − 2e$^-$ ⟶ ZnO − 2H$^+$ emf = 1.25 Volts cathode: PbSO$_4$ + H$_2$O + 2e$^-$ ⟶ PbO$_2$ + 2H$^+$ emf = 1.68 Volts The cell can be recharged by applying an external voltage source which reverses the arrows and the signs of the electron and the proton terms.

EXAMPLE 25

The membranes of the present invention may be employed to make a conventional "drycell" battery completely rechargeable. Conventional drycell or alkaline batteries are not fully rechargeable because zinc diffuses into the manganese dioxide over time and is not recoverable during the charging cycle, thereby poisoning the manganese dioxide. A commercial Leclanche drycell battery was disassembled and the paper separator was replaced with a membrane constructed of 30% Union Carbide Corporation 4,000,000 molecular weight polyethylene oxide sold under the trade name "polyox 301" and 70 percent Dow Chemical Corporation polyvinylidene chloride sold under the trade name "Saran 864 resin". The latter modified cell was found to deliver a current equal to the conventional dry cell. In addition, the modified cell could be repeatedly deeply discharged and charged, limited only by irregular replating of the zinc.

EXAMPLE 26

The use of the membranes of this invention allows the use of fuels such as sugar, alcohol or carbon in batteries or fuel cells at room temperature. For instance, a cell consisting of a membrane prepared from 25 percent Union Carbide Corporation 4,000,000 molecular weight polyethylene oxide sold under the trade name "Polyox 301" and 75 percent Dow Chemical Corporation polyvinylidene chloride sold under the trade name "Saran 864 resin", separating a 5N KOH anolyte and a catholyte consisting of saturated sucrose solution with 10% nitric acid, was tested as a battery. When a platinum electrode was used in the catholyte and zinc used as the anode, an open circuit voltage of 2.4 volts was obtained with a cell resistivity of about 3 Ohm-cm$^2$. When platinum was used in both electrolytes, an open circuit voltage of 1.1 volts was obtained with a cell resistivity of about 28 Ohm-cm$^2$. If the catholyte is replaced with a saturated solution of strontium nitrate with 10% nitric acid with a carbon cathode and the anolyte replaced with a 5N KOH solution saturated with K$_3$PO$_4$ and a platinum anode, an open circuit voltage of 2.5 volts is obtained with a cell resistivity of about 3 Ohm-cm$_2$.

EXAMPLE 27

Another application of a membrane in accordance with the present invention is in "flow" batteries which employ the change in valence of two metal ions in two electrolytes connected with a membrane. One of the metal ions is oxidized while the other ion is reduced during charging and the reverse takes place during the discharge process. An experimental iron//copper battery employed a 30% iron sulfate and a 20% copper chloride electrolyte. The electrolyte was separated with a membrane of the present invention. The membrane was composed of 30% polethylene oxide in a polyvinylidene chloride matrix. The experimental battery had a carbon anode and a steel cathode. The experimental battery produced about 10 watt hours per gallon of electrolytes or approximately 1.2 watt hours per pound.

It is known that an emf is developed between two electrodes placed in two different electrolytes when separated by a membrane. This phenomenon is well recognized and is quantified by the Nernst equation of physical chemistry which relates an emf to the log ratio of the activities of the two different electrolytes. The activity is nearly equal to the concentration of an electrolyte so a membrane can be used to measure concentration differences or the developed emf can aid in certain electro-chemical processes. The theoretical emf according of the Nernst equation for single electron reactions at room temperature is 0.059 volts per factor of ten difference in activities or concentration. Conventional pH sensors use a thin glass membrane which passes only protons to measure the concentration difference of proton of hydrogen ions on either side of the glass membrane. The voltage change of the most pH measuring cells is slightly above 0.05 volts per factor of ten change in the measured electrolyte concentration. If the fragile glass membrane is replaced with a membrane of this invention, the same voltage to concentration relationship is found, but with other advantages.

The glass membrane used in pH probes cannot pass significant current thereby requiring expensive high input impedance voltmeters. To minimize polarization effects, bulky and complex reference electrodes and electrolytes are required.

EXAMPLE 28

A simple pH measurement cell was constructed of a membrane as described in Example 2 above. The membrane separated a standard electrolyte of 0.1N H$_2$SO$_4$ and the solution to be tested. Two identical stainless steel wires of 0.023 cm were cleaned and used as the two electrodes. The slope of the voltage/decade concentration change was equal to 0.052 volts/decade which is comparable to present state of the art of pH measurement probes. Since the membrane is capable of passing considerable current, the stainless steel wires can be "cleaned" or depolarized with a controlled electrical current prior to usage.

The pH, concentration or activity differences can be measured using the membranes of this invention with a reversible current source and a low impedance voltmeter. The difference in the cell voltage as a constant electric current flows first in one direction through the cell and then in the other through non-reactive electrodes, is proportional to the concentration difference. The difference in voltage is equal to twice the emf across the membrane.

EXAMPLE 29

Free chlorine in solution was measured in two electrolyte cells using a membrane according to Example 2 above and with measurements of the open circuit voltage. In this case, a reference electrolyte was used. The reference electrolyte consisted of a saturated solution of $K_3PO_4$ brought to a pH of 3.4 by adding phosphoric acid. An electrode of 50% tin and 50% lead was placed in the reference electrolyte. The unknown solution consisted of varying the concentration of a sodium hypochlorite solution. The unknown solution had a copper electrode. This example yielded a slope of 0.068 volts/decade. The increase in slope may be due to the use of an "active" cell wherein the cell functions as a battery with protons flowing rather than in the normal "passive" type cells currently in use.

EXAMPLE 30

The materials of this invention can be used as membranes to change the pH of solutions as exemplified by the following demonstration which causes a change in color to occur in an electrolyte when an electrical current is passed through a cell using the membranes of this invention. The membrane was constructed of: 37% hydroxyethyl cellulose, as Cellosize* QP4400-H supplied by Union Carbide Corporation, 12.5% lignin sulfonate, Lignosol* FTA supplied by Reed Lignin, Inc. and 50.5% polypropylene resin supplied as Pro-fax PC072 by Himont U.S.A., Inc. The ingredients were melt/mixed at about 180 Celcius and formed into a sheet of about 0.02 cm thickness and then soaked in water for about 24 hours. The membrane separated two electrolytes which were both a 10% $K_2HPO_4$ and 0.02% phenolphthalein solution. When an electrical current was passed through the two electrolytes using platinum electrodes, the pH of the catholyte (negative) would increase and the red color would appear, whereas the pH of the anolyte would decrease and its color would disappear. A pH difference of more than 2 pH points could readily be obtained and remained constant for weeks. The effect could readily be reversed by applying a reverse electrical current allowing each electrolyte to alternate between being a clear or red colored solution. Such a phenomenon is useful for display devices and different colors can be obtained by using different pH indicators or pH sensitive dyes and the like.

EXAMPLE 31

The flow of protons can change the pH of both electrolytes with the anolyte becoming more acid with a decreasing pH while the catholyte becomes more alkaline with an increasing pH. A cell using a membrane described in Example 2 and containing two identical smooth platinum electrodes both immersed in distilled water with an initial pH of 4.6, was connected to a 10 volt source. The catholyte reached an equilibrium pH of 5.7 while the anolyte developed a pH of 2.5. The difference in pH remained constant for hours during the test with discontinuance of the electrical current, but could be reversed with a reversed current flow yielding the same values in the new anolyte and catholyte. The explanation for this unexpected result may be due to reversible electrochemical reactions with absorbed $CO_2$, the formation of $H_2O_2$ or absorption of ions on the surface of the membrane.

The membranes of the present invention may be used with electrolyzers and other electrochemical cells so that added efficiencies may be obtained by operating each half cell in the optimum pH electrolyte. By operating the hydrogen generating electrode or cathode in an acid and the oxygen electrode in an alkaline electrolyte, the voltage necessary to electrolyze water can be significantly reduced to a theoretical emf of 0.41 volts ($2H+ + 2e- = H_2$ at 0.0 volts, and $4OH- = O_2 + 2H_2O + 4e-$ at 0.41 volts). Two unexpected phenomena were observed in attempting electrolysis at reduced voltage using the membranes of this invention: The first is the ability to maintain a constant current which would not be possible without a chemical reaction between the acid and base and the second is the reversibility of the chemical reaction. If (for instance) a concentrical permselective cationic membrane were used, the alkali metal ion could diffused through the channels of the membrane and react with the acid in the catholyte forming a salt. Such a reaction would not be reversible. The use of the membranes of this invention allow the transport of both anions and cations resulting in a reversible reaction. The electrolysis of water with less electrical energy than the Gibbs free energy can only be obtained with the coupling of chemical energy to the electrochemical reactions. Some of the unexpected results of using the membranes of this invention are summarized in FIG. 2 which represents the current/voltage curves of a typical electrolyzer cell using the membrane of example 5 above or from a melt/blend of acrylic acid bound to carbon in an inert matrix such as: 37% acrylic acid of molecular weight of about 4,000,000 (Carbopol 940, a product of B.F. Goodrich Company); 10 percent activated carbon powder sold under the trade name "Vulcan XC 72R" by Cabot Corporation; and 53 percent polypropylene resin sold under the trade name "Pro Fax PC072". Smooth unblackened platinum electrodes are used to eliminate additional emfs caused by electrode/electrolyte interactions.

Figure 2:
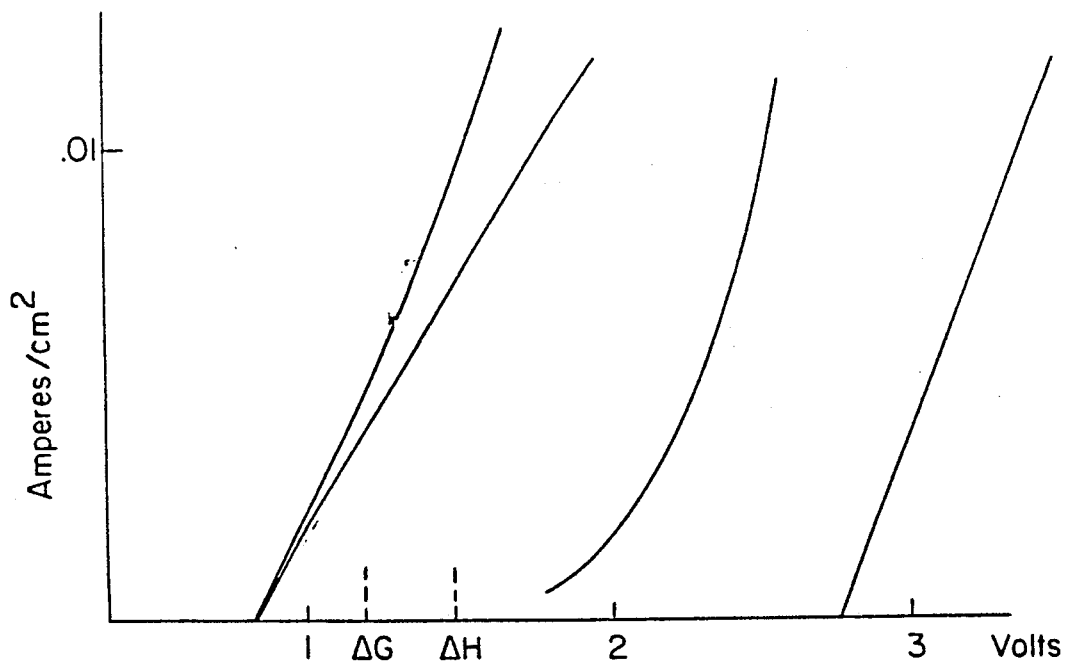
FIG. 2 is a graph illustrating the current vs. voltage relationship for an electrolyzer cell employing a membrane in accordance with the present invention.

FIG. 2 shows a cell operating at less than the heat of formation (delta H) which is about 1.5 volts and less than the Gibbs free energy (delta G) of about 1.2 volts when the cell is 1) operated at low current density levels, and 2) with an acidic catholyte and a basic anolyte. Curve 40 shows the unexpected linear current versus voltage curve as the cell is first energized with the reduced intercept voltage less than the theoretical minimum voltage (free energy) for electrolyzing water. If the voltage is reversed, as shown in curve 50, a much higher voltage is required (the theoretical emf is 2.057 volts: $H_2O + 2OH- = \frac{1}{2}H_2 + e-$ at 0.828 volts plus; $2H_2O = O_2 + 4H+ + 4e-$ at 1.229 volts), but the resistance of the cell is slightly lowered with the current linear with respect to the applied voltage. If the temperature is increased to 50 degrees Celcius, with the current flow in the initial direction, the resistance of the cell drops indicating an activation energy greater than 9 kJoules/mol as shown in curve 60. The electrolysis at less than 1.2 volts indicates an electrochemical reaction other than the expected and analysis of the electrolytes indicates that the following complex reversible electrochemical reaction occurs:

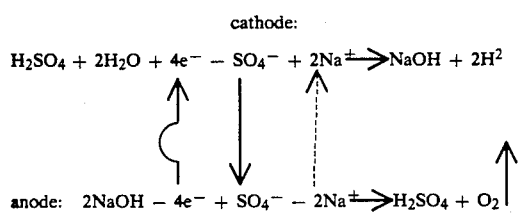

where the sulfate and sodium ions traverse the membrane while the electrons are transferred with the applied current. If the current is reversed, the sodium and sulfate ions return to their original electrolytes and the pH of each electrolyte approaches the original value as may be diagrammed.

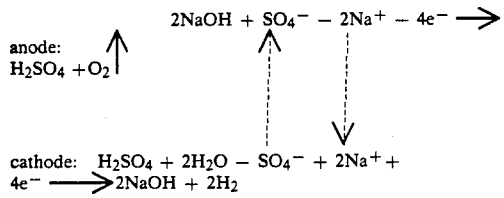

The simultaneous transfer of both anions and cations through the membrane results in the transfer of chemical energy between the two electrolytes which is equated to the energy of the electron transfer. The membrane serves, therefore, as a coupler in the conversion of electrical energy into chemical energy or vice versa. The production of an acid, and base with the hydrogen and oxygen is not expected and may be explained because of the novel coupling of the chemical energy of the acid/base reaction to the electrochemical reaction and vice versa.

It is to be noted that such a reverse reaction could not take place with a commercial permselective membrane since only ions of one charge could diffuse through the membrane. For the reverse reaction above, more electrical power is supplied than for the forward reaction.

An electrolyzer cell using a membrane constructed of melt/blended 30% polyethylene oxide of molecular weight 600,000 sold under the trade name of "Polyox 205" by Union Carbide Corporation and 70% polyvinylidene chloride resin sold as "Saran 864" by Dow Chemical Corporation, and platinum electrodes, and filled with 1N $H_2SO_4$ in the catholyte and 1N KOH in the anolyte; showed the reversal in the pH with current flow indicating the exchange of the acid and base with the rate as expected by Farraday's law and the above explanation.

The "normal" exponentially increasing current versus voltage curve is shown in curve 70 when both of the above electrodes are in a 1N NaOH electrolyte without a membrane. As the cell with the membrane operates, the pH of both electrolytes shift toward each other and then reverses, but if the current is reversed, the pH of each electrolyte can be returned to its original value.

The effect of varying the hydrogel content and the effect of temperature upon the voltage-current relationship is shown in Table 4 where "V forward" is at least squares fit to the data obtained from the current voltage measurements. The initial voltage is, therefore, the first term and the resistance is the slope or multiplier of the current I. The catholyte in all cases is 1M $H_2SO_4$. The membrane area is 8 $cm^2$. The area of each platinum electrode is 3.3 $cm^2$ with each electrode about 1 cm from either side of the membrane. The voltage is measured as the current is varied from 0.005 to 0.100.

TABLE 4

| Sample | Anolyte | Temp −C. | % HYD | V Initial |
|---|---|---|---|---|
| 1 | 1M KOH | 25 | 20 | 0.96 + 150*I |
| 2 | 1M KOH | 25 | 25 | 0.98 + 18*I |
| 3 | 1M KOH | 25 | 30 | 1.00 + 10*I |
| 4 | 1M $NH_4OH$ | 25 | 30 | 1.36 + 17*I |
| 5 | 1M $NH_4OH$ | 31 | 30 | 1.32 + 15*I |
| 6 | 1M $NH_4OH$ | 47 | 30 | 1.20 + 12*I |

The rate of transport of different ions through the materials of this invention appears to be closely proportional to their conductance at infinite dilution in water. An experimental cell was constructed using a membrane constructed of 22 percent Union Carbide Corporation 4,000,000 molecular weight polyethylene oxide sold under the trade name "Polyox 301"; 11 percent activated carbon powder sold under the trade name "Vulcan XC 72R" by Cabot; and 67 percent polypropylene resin sold under the trade name "Pro-Fax PC072" by methods outlined above. The anolyte was a 4% NaOH and 5.6% KOH solution while the catholyte was a 10% $H_2SO_4$ solution. Platinum was used as the electrodes. Three samples were collected after three different elapsed ampere hours and analyzed. Potassium was found to be transported at a ratio of 1.6:1 to sodium which approaches the ratio of 1.5:1 for their ratio of conductances at infinite dilution in water. Similarly, copper is found to approach the 6.4:1 ratio of hydrogen to copper conductance at infinite dilution in water.

Fuel cells can also have an increased electrical output by coupling the chemical energy of two electrolytes. For instance, if the anolyte is made alkaline and the catholyte made acidic for the normal hydrogen-oxygen fuel cell, then the theoretical voltage is increased from 1.2 to 2.0 volts with the following half cell reactions:

| anode: | $H_2 + 2 OH^-$ | $2H_2O + 2e^-$ | 0.828 volts |
| cathode: | $O_2 + 4 H^+$ | $2H_2O - 2e^-$ | 1.229 |
| total cell emf | | | 2.057 volts |

The electrochemical reactions can be diagrammed as"

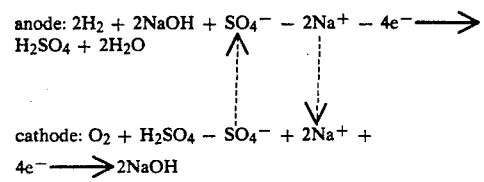

As explained for the electrolyzer above, the increase in cell voltage is due to the added chemical energy of the acid and base. After the acid and base have reacted, they may be regenerated by applying an electrical current. A cell made with the membrane of example 5 above and with 20% NaOH in the anolyte and 10% H₂SO₄ in the catholyte and with unblackened smooth platinum electrodes, yielded 2 volts open circuit when the electrodes were covered with hydrogen and oxygen.

EXAMPLE 32

One important aspect of the present invention is the ability of the ionic semiconductor materials to split water into its composite ions. This ability is exemplified by the following experiment. Two identical strips of platinum, each with an active area of 0.3 cm² area, were selected as electrodes with one of the platinum strips being covered with an ionic semiconductor prepared from 30% Polyox 301 (Union Carbide), 20% phenol-formaldehyde 12704 (Durez) and the remainder being polypropylene (Hooker Chemical). The constituents of the ionic semiconductor were melt-mixed and pressed to about 0.5 mm thickness. The two electrodes were placed together in a 50 ppm sodium hypochlorite solution at room temperature and the open circuit voltage as well as the voltage when connected to a 100,000 ohm load were recorded.

A voltage of over 50 millivolts could be maintained at room temperature with the resistive load connected, indicating that a continuous current was being produced. The open circuit voltage was about 0.2 volts. Heating the cell to about 50 degrees C. raised the open circuit voltage to 0.5 volts and the voltage across the 100,000 resistor to 0.25 volts demonstrating a significant increase in power output with increased temperature.

The following novel "water splitting" reaction at the ionic semiconductor covered anode is assumed to explain the continuous current production and high activation energy or temperature dependence. (The double slash, //, is used to indicate the nonporous junction with the ionic semiconductor and the ion and electron transfer between the two half cells is indicated by lines drawn between the two electrode equations.)

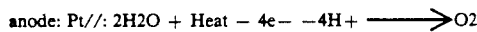
anode: Pt//: 2H2O + Heat − 4e− −4H+ ⟶ O2

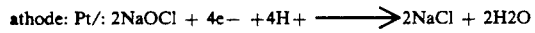
athode: Pt/: 2NaOCl + 4e− +4H+ ⟶ 2NaCl + 2H2O

If the experiment is repeated without the ionic semiconductor coating on the one platinum strip, no voltage or current is observed.

The novel results can be explained by assuming that a water molecule in the presence of the bound hydrogels and with sufficient thermal energy is able to 'split' into its constituent ions. Increasing the temperature increases the numbers of water molecules with sufficient thermal energy to split. Such a high concentration of splitting is normally not encountered except under high electrostatic fields or in the presence of high pressure and temperature with a catalyst. Further examples of water splitting are given in some of the following examples.

EXAMPLE 33

Films formulated from a flexible matrix material and a hydrogel according to the teaching of this invention are useful for providing a protective and 'breathable' interface between the dermis or epidermis of a body and the ambient environment. The membranes of this invention are believed to function in a manner similar to natural biological membranes and are 'breathable' or can pass perspiration or body exudates at or in excess of the normal rate of production of the body; are bioadhesive or can bond to the epidermis or dermis; provide 'active' oxygen or protons through water splitting; and can be bonded to a supporting fabric. All of these characteristics are acheived while providing a protective barrier to rain, chemical hazards, infectious material or agents, dirt etc.

The film may be applied to the skin or subdermal flesh by means of the direct application of a fluid which contains the solid constituents which form the film on drying or by the direct application of a preformed film either pre-moistened or moistened by the exudate of the subdermal flesh. The film can be kept in place for days without the expected formation of an exudate interface or scab since the film, because of its tight adherence to the dermis, functions as would the natural skin. It is believed that the film also furnishes ions through water splitting (as discussed in Example 32) which aids in faster healing of the wound. If the films are flexible and thin there is no sense of discomfort and very little awareness of its presence.

The film may also be applied adjacent to the skin by either a standard wound type dressing, wherein the film is either self supporting, or through use of a composite of the film with a supporting structure that holds the film adjacent to the body.

The film may also be as a stand alone film or incorporated on or in a fabric which provides protection for the body or parts of the body such as in outer garments for rain protection or completely closed garments such as worn for environmental protection against hazardous chemicals and the like.

The advantages of this novel protective film are therefore: the ability of the film to be: 1) self adhesive either to the epidermis or dermis or to a supporting fabric or matrix with suitable initiation by water, heat or pressure, 2) compatible with the processes of the body, 3) able to transport water equal to the normal exudate rate of the body, 4) sufficiently strong to provide mechanical protection, 5) impenetrable by unionized matter, 6) able to provide hydroxyl or hydrogen ions for tissue rebuilding, and 7) of low inherent cost.

A liquid ionic semiconductor formulation incorporating a flexible matrix and a hydrogel is as follows: 4 grams hydroxyethylcellulose or HEC as 'Cellosize' QP 100000-H as supplied by Union Carbide. 94 grams polyurethane dispersion as 'NeoRez R- 963' supplied by Polyvinyl Chemicals which contains 34% by weight of polyurethane. The HEC is ideally first dissolved in water and then added to the liquid urethane mixture during mixing. Water must generally be added since the HEC is a thickener and otherwise the mix would be too thick. (It should be noted that hydrogels have been added to coating solutions in the past to control the viscosity, but in these cases the amount of added hydrogel was been at a considerably lower lever (typically less than 1%) than is used in ionic semiconductive materials.)

Hydroxyethylcellulose, HEC, can be added and mixed with the polyurethane to form a non-leaching membrane. One advantage in using HEC in polyurethane is that a 'non-blocking' or non-sticky film can be obtained. Most urethane sheets have blocking and will adhere to themselves to some degree which results in a 'tacky' feeling of the urethanes. Films formed from HEC and polyurethane provide a silky soft film which is a strong advantage for clothing or garment applications.

Polyurethane has been discovered to provide sufficient bonding to many of the hydrogels so that additional coupling agents and the like are not required. An example of urethane functioning as a coupling agent is provided in the following example of a solid plastic capable of being extruded or formed with conventional plastic equipment:

1 gram of polyethylene oxide supplied as Polyox C014 by Union Carbide, 0.5 gram of urethane (ester based) solid resin supplied as Q- Thane PS455-100 by K.J. Quinn and Co., and 2 grams of polyvinylidene chloride supplied as Saran Resin 864 by Dow Chemical were dry mixed together, melt mixed at about 350 degrees F. and then extruded in a sheet of about 0.02 inches thickness. The sheet was found to absorb about its own weight in water with a conductance of less than 20 ohms-cm$^2$ in a Cu/CuSO4/H2SO4/Pt test cell as described earlier. The novel membrane has no detectible copper passage after one hour of operation.

A very good liquid film can be produced using Pectin. The following formulation is by dry weight of the active ingredients and not of the emulsion or solution weight. The final dried film consisted of about 25% by weight of Pectin. The formula consists of: 20.8 parts vinyl acetate/ethylene supplied in an emulsion from Reichhold as Elvace 1870, 5.2 parts of Pectin supplied in a solution by General Foods Corp. under the name Certo. The ingredients were mixed together in a high speed mixer to a uniform consistency and then coated on a substrate or cast as a free standing film.

The physical characteristics of a film in accordance with this invention are essentially those of the supporting plastic matrix unless the film is saturated with water, in which case there is expansion, softening and whitening similar to natural human skin.

Thin films as described above can be constructed having water vapor transmission rates greater than 3000 grams/day-m2 when measured by ASTM E 96-80 Procedure B. It should be noted that the vapor pressure differential in the above test which drives the water vapor through normal porous materials is not required for the films of this invention. The water transmission rates of the films of this invention are limited in general by the rate of water removal or evaporation rather than by water 'take-up'. For instance, if a polyurethane film as described above is brought into contact with water, it can exhibit a water absorption rate much greater than 5000 grams/day-m$^2$ at 100 degrees F. Since the energy for ion transfer is thermal, there is a strong temperature coefficient for the absorption rate.

The films of the invention can be produced with a wide variety of supporting plastics as well as with varying amounts of added active polymers to vary the water vapor transfer rate or the resistance to water swelling.

Pigments can be added to the ionic semiconductor materials to match normal skin coloration such that the materials can be used for cosmetic rebuilding, covering of skin defects or normal cosmetic purposes.

EXAMPLE 34

Selective proton or hydroxyl transfer through the novel membranes of the invention can be obtained by providing an inert hydrogel depletion junction between the membranes and the external liquid which serves as a barrier for all but protons and hydroxyls. Such a junction consists of a thin layer of a matrix material functioning as a thin hydrogel deficient region perhaps corresponding to an 'intrinsic' conduction region in electronic semiconductors.

For example, Kraft paper can be coated with a solution consisting of a 40% polyethylene (Union Carbide 301) and a 60% Phenolic (Durez 12704) prepared as described in Example 9. After the mixture has dried but not fully cured, it is coated with an additional thin layer of phenolic, dried and then the combined films cured.

The double coated paper was then tested in the preceding Cu/CuSO4//H2SO4/Pt test cell for both conductance and copper transfer through the novel membrane.

The (dc) conductance of the combination was not quite as good as would be obtained with just the novel membrane coating, which is about 10 Ohm-cm$^2$, but was nonetheless quite good at about 80 Ohm-cm$^2$. The copper transfer was immeasurable after 2 hours, compared with about a 6% rate for the single uncoated film.

A phenolic film without the hydrogel/phenolic coat would not be expected to pass a significant electical current.

The conclusion is, therefore, that the novel membranes split water, as assumed, and the protons are able to be pass through the phenolic. If the current is reversed then hydroxyl ions are passed through the novel membranes.

For membranes formed as described in preceding examples, increased selectivity for protons may be explained by the formation of an outer 'skin' of the matrix material with a lower hydrogel content than the body of the membrane during fabrication.

EXAMPLE 35

The membranes of this invention may be used to provide a novel method of purifying water. Since the ions of water have many times the transfer rate of other ions, membranes constructed according to the teachings of this invention can be used to reduce the impurity content of water. Since the membranes are depletion driven, purified water can be absorbed from one side while contaminated or salt water can be made available at the other surface. One application would be in supplying water for crops by pumping sea water or polluted water through tubes or troughs made or coated with the films of this invention which are placed under ground or adjacent to the root systems of the plants or crops to be irrigated. The novel membranes have the capability of providing purified water only as needed to the roots or soil leaving the bulk of the salt behind in the main stream of water.

The membranes of this inventions will transport water only as long as water is being removed from one surface and supplied at the other. The rate of transfer of the water is a function of the temperature (being increased with increased temperature), the rate of removal of the water from the purified side, and the percentage of hydrogel in the membrane.

Films with a thickness greater than 0.005 cm or so can be easily evaluated for a conservative comparative water transmission (assuming an infinite drain) by measuring the rate of water take-up as well as by total water absorbed. The standard water vapor penetration tests like ASTM E 96-80 are not directly applicable since the pressure difference between the heated interior of the container and the ambient cannot drive water vapor though the non-porous ionic semiconductors. The preferred measurements consist of measuring the area of and weighing (1) the sample as prepared, inserting the sample in water heated to about 40 degrees Celcius for one minute, blotting dry, weighing (2) and inserting again in water for two minutes, blotting dry and weighing (3), and then leaving the sample in the water for several hours or until absorption is complete and then blotting dry and weighing (4). The difference in weight between weighings (2) and (3) is divided by the area of the sample, multiplied by 720 (weight gain/cm$^2$ in 24 hours) times 104 to obtain grams per 24 hours per square meter. This number is divided by two to obtain the water transmission rate for one side. The total water take-up is expressed as the ratio between weights (1) and (4) or (1)/(4).

Table 5 below lists some results:

TABLE 5

| % wt. | Hydrogel | Matrix | Rate g/m2-day | Ratio dry/wet |
|---|---|---|---|---|
| 25 | HEC | Urethane A | 15,000 | 0.41 |
| 20 | HEC | Urethane A | 9,000 | 0.53 |
| 20 | HEC | Urethane B | 33,000 | 0.29 |
| 20 | Starch | Vinyl acetate | 12,000 | 0.60 |
| 20 | Pectin | Vinyl acetate | 20,000 | 0.57 | where:
HEC is hydroxyethyl cellulose as 'Cellosize' QP 100000-H supplied by Union Carbide.
Starch is 'ARGO' corn starch supplied by Best Foods
Pectin is supplied in a solution under the trade name 'Certo' by General Foods Corp.
Urethane A is a polyurethane dispersion 'NeoRez R-963' supplied by Polyvinyl Chemicals
Urethane B is a polyurethane dispersion 'NeoRez R-966' supplied by Polyvinyl Chemicals
Vinyl Acetate is a vinyl acetate/ethylene emulsion supplied by Reichhold as 'Elvace 1870'.

It should be noted that the above tests do not indicate the maximum rate of water take-up since that would occur during the first moments of insertion in the water. In applications of the above formulations, the limitations have not been found to be the rate of water take-up, but rather the rate of water removal from the drier side of the film.

The first item in the table, 25% HEC/Urethane A, with the rate of 15,000 g/m$^2$-day compares with the rate of 3,000 g/m$^2$-day when measured by the ASTM E 96-80 Procedure B. The difference is believed to be due to the limited rate of evaporation from the exposed surface of the ASTM test. The 25% HEC/Urethane A film is also an excellent electropermeable membrane with a dc resistance of less than 6 ohm-cm$^2$ with a dc current density of about 7 mA/cm$^2$ when separating an acid 20% copper salt analyte and a 10% sulfuric acid catholyte. The copper ion transport is less than 2% of the total ion transport. For a comparison, 20% Pectin/vinyl acetate film has a dc resistance of 5 ohms-cm$^2$ and a copper ion permeation equal to 4% of the total charge.

Other ions such as sodium and chlorine from salt may also be transported through the membranes of this invention at lower transfer rates. For some crops and locations the amount of salt passing through (less than 10% of main stream content) may in practice be low enough to be of no concern or even desireable for the mineral supply of the crops.

If a higher purity of water is desired, a thin coating of a matrix material can be applied as described in Example 34.

An example uses two plastic tubes sealed at one end with the formulations described in Example 34 above. The tubes were placed upright upon absorbent toweling with the membranes of this invention in contact with the toweling. The tubes were filled with water and the open upper ends of the tubes were sealed. The tubes were weighed at different times to determine water loss into the toweling which was assumed to function as absorbent soil.

The tube with the phenolic added coating had a transfer rate of nearly pure water of about 350 grams per day per square meter at room temperature. The second tube without the added phenolic coating transferred water at the rate of about 1500 grams per day per square meter.

If one assumes that novel membranes for this application have a life of 10 years and can be film extruded to form practical water troughs or tubes at a cost of less than $0.20 per square meter, then the cost of delivered purified water from the first the novel membranes is about $160 per million liters ($0.60 per thousand gallons) and the cost of less pure water from the second the novel membranes is about $36 per million liters ($0.14 per thousand gallons) which is significantly less expensive than existing methods.

EXAMPLE 36

This example relates to an improved hydrogen electrode and applications thereof. Hydrogen electrodes have been used to provide a source of hydrogen ions in electrochemical reactions or measurements and have consisted of a simple electrode assembly wherein hydrogen gas is bubbled up on the surface of platinum or constructed of a complex porous electrode assembly perhaps typified by an electrode assembly and its applications as described by Juda et al in U.S. Pat. No. 4,614,575.

The hydrogen electrode can take several forms. Thus, the electrode can consist of a conductor coated with an ionic semiconductor wherein the semiconductor behaves as both a solid electrolyte and the water splitting element. Alternatively, the electrode can comprise an assembly wherein an electrolyte is disposed between the the semiconductor and the conductor.

The novel hydrogen electrode of this invention differs markedly from the existing hydrogen or gas diffusive electrodes in that the existing electrodes require the continual introduction of hydrogen gas into ideally a porous catalytic anode whereas the electrodes of this invention rely upon water splitting at the surface of an ionic semiconductor to supply hydrogen ions and no hydrogen gas is required. A further advantage is that the anode does not have to be a catalyst and poisoning of the electrodes is not a problem.

An experimental cell was constructed with two chambers which were separated by an ionic semiconductor which was obtained from a coated nylon fabric with a film prepared from the following formulation: 60 g poly(ethylene oxide), supplied as Polyox 301 from Union Carbide; 40 g phenolic resin, supplied as 12704 from Durez; 200 g PVDC latex, supplied as RAP 184 from Dow Chemical Corporation. The poly(ethylene oxide) and phenolic are first dispersed in 2-ethoxyethanol and then mixed together with water under a high shear to form an associated product and then the latex is added and mixed together. The coated fabric was dried and then heated to cure the film.

A 5% KOH solution anolyte and a platinum anode were placed in one chamber. The catholyte contained a 5% sulfuric acid solution to which was added copper sulfate to obtain an initial solution strength of about 800 ppm of copper. An aluminum electrode was inserted as the cathode. A constant current was applied to the cell of about 10 mA per square centimeter of the ionic semiconductor producing a minimum cell resistance of about 200 ohms-square centimeter of the ionic semiconductor. The voltage dropped initially quite rapidly and then slowly increased as the copper was plated out of the catholyte onto the cathode. The voltage of the cell started at about 1.4 volts, dropping and then finally reaching about 2 volts when the experiment was stopped. After 45 minutes, the aluminum was weighed and the weight gain indicated the removal of the inserted copper.

Without the separating membrane little copper can be plated out even at low current efficiency.

The above cell and this invention can described by the following diagram and electrochemical equations which relate to the removal of dissolved metals in water.

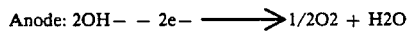

Anode: $2OH^- - 2e^- \longrightarrow 1/2 O_2 + H_2O$

Membrane: $2H_2O \longrightarrow 2H^+ + 2OH^-$

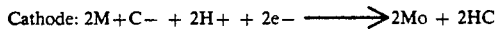

Cathode: $2M + C^- + 2H^+ + 2e^- \longrightarrow 2Mo + 2HC$ where $M+$ is a metal ion and $C-$ is the associated complex. The above electrochemical reactions were written for a metal ion of valence one, but it should be understood that the reaction would also apply for other positive ions or other valences.

The catholyte side of the membrane can be seen to be functioning as if a conventional hydrogen electrode were being used injecting hydrogen ions into the electrolyte. Since the membrane is non-porous, other ion exchanges at the anode are negligible as for instance, the C-complexes are prohibited from passing through the membrane.

The use of the KOH solution in the above experimental cell illustrates another advantage of using the novel hydrogen electrode assembly since the operating voltage can be reduced resulting in lowered electrical power requirements by utilizing the entropy increase of KOH as described in Example 31. It should also be obvious that other combinations of electrolytes can also be used.

EXAMPLE 37

It has been discovered that the novel membranes containing an electrically conductive element or a current collector may be used to replace porous oxygen or gas electrodes for electrochemical cells. Such electrodes, when interfacing with air or oxygen, reduce the oxygen and transfer the ions to the electrolyte.

The prior porous gas electrodes use porous conductive materials made form or coated with catalytic materials such as platinum which enhance the reduction of oxygen. The first such electrode made over a hundred years ago, consisting of mixed carbon and platinum powder, is still exemplary of the existing gas electrodes.

The conductive membranes of this invention differ considerably from the prior art in that they are non-porous with the initial ionization of the gas, ion transport, electron transfer, and ionic injection assumed to take place in four different areas and medias, (1) the gas/membrane interface, (2) The interior of the membrane, (3) the membrane/conductor interface, and (4) the novel membrane/electrolyte interface.

A conductive membrane may be constructed by coating a porous electrical conductor with an ionic semiconductor material such that the composite is rendered non-porous or the voids are filled with the added material. It is preferable that the conductor is covered on both sides. For example, a perforated platinum sheet or a stainless steel screen can be sandwiched between two sheets of a thermoplastic membrane with heat and pressure, or the conductors can be coated with a water or solvent based dispersion or solution to form a covering.

A formulation which can be used to form thin membranes (films) for the application being described is as follows:

Three grams of polyvinylidene fluoride as supplied by Ugine Kuhlman of America Inc. as Foraflon 1000 LD was dissolved in 10 ml of N-methyl 2 pyrollidone. 1 gram of polyethylene oxide as supplied by Union Carbide Corp. as WSR Coagulant Polyox and 0.5 gram of polyacrylic acid as supplied by BF Goodrich as Carbopol 940 were dissolved in 30 ml of N-methyl 2 pyrollidone and mixed under high shear to form an associated product. The two dissolved materials were finally mixed together and sufficient solvent added to form the proper viscosity.

Variations of the matrix may be other dissolved polymers such as polysulfone as supplied by Union Carbide as P-1700, a polyvinyl chloride resin supplied by Borden Chemical as VC 440, polyvinylidene chloride supplied by Dow Chemical as Saran 864. Other hydrogels can also be used with appropriate coupling agents such as polyurethane.

One of the above films is coated on a conductive porous material such as a non-woven carbon cloth obtained as 0.5 ounce/square yard 100% carbon fiber (1" long) from International Paper Company to form a conductive electrode.

A simple zinc/air battery offers an example of the application of the novel non-porous conductive membrane. The battery is constructed using one of the above novel conductive membranes as the oxygen or depolarizing electrode. This conductive electrode separates a 10% KOH analyte containing a smooth metal zinc electrode and the ambient air. The effective area of the zinc and novel conductive membrane are of about 6 cm² area each. The electrodes are separated by about 1 cm.

At 24 degrees Celcius, the open circuit voltage of the cell is 1.2 Volts with an internal resistivity of 2400 ohms-cm² (equal to load resistance to drop cell voltage to ½ of open circuit voltage). The maximum relatively continuous power output is about 0.1 mW per cm² of the novel conductive membrane.

When the cell is heated to about 60 degrees Celcius, the open circuit voltage remains at 1.2 volts, but the cell resistivity decreases to about 1000 ohms-cm². With a maximum continuous power output of about 0.4 mW per cm².

The resistance of the heated cell above can be further reduced by over 30% by passing pure oxygen over the outer surface of the oxygen electrode indicating the consumption of oxygen within the cell.

If instead of adding oxygen to the outside of the air electrode, it is bubbled into a solution of 10% sulfuric acid which in turn is in contact with the novel conductive membrane by means of another added compartment, the open circuit voltage at room temperature remains nearly the same at 1.2 volts, but the cell resistivity drops to about 700 ohm-cm$^2$ with a continuous power output of about 0.5 mW/cm$^2$.

If the above cell with oxygenated sulfuric acid is heated, the cell resistivity drops proportional to temperature being about: 600 ohm-cm$^2$ at 29° C., 480 ohm-cm$^2$ at 36° C., 430 ohm-cm$^2$ at 44° C. and 400 ohm-cm$^2$ at 53° C.

Another unexpected result occurs when a small carbon rod with a 2 cm$^2$ area is inserted into the heated oxygenated sulfuric acid example above and electrically connected to the conductive membrane. The cell voltage increases to 1.4 volts and the resistivity lowers further to about 300 ohm-cm$^2$ and delivers a relatively constant power of about 1.7 mW/cm$^2$ at about 60 degrees Celcius.

The results from this example are not expected since the connection of an external electrode to the air electrode would not be expected to change the cell operation and certainly not to improve the operation of the cell.

A further modification of the air cell results when the zinc anode of the above heated cell is replaced with a carbon electrode in a sugar saturated 10% KOH solution. The cell is therefore: C/KOH-sucrose//C//H2SO4-O2/C. Where the //C// represents the novel conductive membrane, and the novel conductive membrane is connected to the carbon electrode in the sulfuric acid. Such a cell when heated to 60 degrees Celcius, and with oxygen bubbled through the sulfuric acid, has an open circuit voltage of 0.7 Volts and can deliver a continuous current of 1 mA/cm$^2$ of the novel conductive membrane area with a cell voltage of about 0.35 Volts (representing a resistivity of about 350 ohm-cm$^2$ for the conductive membrane area). Such a cell is in fact a fuel cell operating on readily available and inexpensive materials and illustrates the unique characteristics of the novel conductive membranes.

A comparison of the above novel conductive membrane can be made with other membranes by exchanging the electrodes and electrolytes for a Zn/10%-KOH//C//10%-H2SO4/PbO2. In this example a commercial lead oxide electrode with an effective area of about 2.5 cm$^2$ is used as Well as the above smooth zinc sheet. A polarization curve was run with the membrane potential drop measured with two reference cells placed adjacent to the membrane on either side. The current levels were maintained for two minutes before changing.

| Amperes | 0 | 0.025 | 0.100 | 0.200 | 0.300 | 0.500 V |
|---|---|---|---|---|---|---|
| cell | 3.00 | 2.89 | 2.73 | 2.55 | 2.31 | 1.73 |
| delta-V | 0 | 0.04 | 0.11 | 0.19 | 0.28 | 0.47 |

The membrane resistance is therefore less than 1 ohm or less than 6 ohms-cm$^2$. It should be noted that the cell is capable of delivering over 50 mA/cm$^2$ at a voltage of 2.31 volts or more than 100 mW/cm$^2$ at a voltage well above the standard lead acid battery's open circuit voltage.

EXAMPLE 38

The novel ionic semiconductive membranes are useful for constructing membrane electrodes since: (1) There is no direct intraelectrolyte contact or exchange. (2) They are capable of maintaining significant current flow with the voltage referenced to the analyte. (3) They have the ability to furnish protons or hydroxyl ions at the junction interface by splitting water molecules with thermal energy. (4) They are highly selective and only respond to redox ions which are electrochemically involved in both electrode reactions. (5) Highly selective electrodes can be obtained by adding an coating of the inert matrix to the junction membrane.

Ionic semiconductive membrane electrodes can be made in two forms. The first, type 1, is similar to the standard reference electrode consisting of an inner half cell but with the junction replaced by an ionic semiconductor separator which can be of any of the formulations listed above. The second, type 2, consists of a metal electrode enveloped with, coated with or contained within an ionic semiconductor material. The ionic semiconductor material in a type 2 electrode functions as a solid electrolyte as well as providing the novel characteristics of the ionic semiconductor. The ionic semiconductor material that is chosen can be based on the bonding capability to the physical support of a probe, the conductance desired, the selectivity, the environment or temperature or ease of fabrication.

Neither electrode is theoretically limited as to size. Since the ionic semiconductor junction is non-porous, no electrolyte reserve for a controlled leakage or buffer is required. Since the ionic semiconductor separator is of relatively high ionic conductance, no area limitations are normally imposed.

The type 1 probe can operate with two different modes. The first mode is the classical, wherein the electrode is oxidized or reduced with an electrochemical reaction yielding or combining with ions which are transferred through the membrane. The second mode of operation involves water splitting at the membrane with a corresponding reduction of protonsor the oxidation of hydroxyl ions depending upon the polarity of the electrode. For a negative reference probe, the second mode can be diagrammed as:

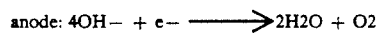
anode: $4OH- + e- \longrightarrow 2H_2O + O_2$

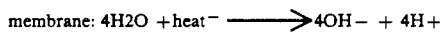
membrane: $4H_2O + heat^- \longrightarrow 4OH- + 4H+$

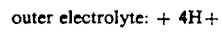
outer electrolyte: $+ 4H+$

The type 2 electrode which can operate also in either mode but may be limited in current density to only a few microamperes per square centimeter if the electrode is not a depolarizer or because of the time for electrochemically generated gasses to diffuse away from the metal-ionic semiconductor junction. The type 2 electrode operates with the ionic semiconductor material serving as a solid (polymeric) electrolyte as well as the ionic semiconductor as above. Miniature type 2 electrodes can be constructed by casting a thin film from a solvent based ionic semiconductor resin onto a thin metal wire or carbon fiber.

A semiconductive membrane electrode of type 1 has been found to be an excellent replacement for commercial reference probes when the inner half cell consists of a Class 1 electrode and the corresponding salt electrolyte. An electrode was constructed by thermal bonding a membrane made as described in Example 13 above to a polypropylene tube with an inner diameter of about 0.4 cm and 6 cm length. The tube was filled with a 3M KCl solution saturated with AgCl. The electrode was a silver strip about 0.3×6 cm which had been electrochemically oxidized in a 10% HCl solution to form an AgCl coating on the silver.

The electrode was compared with commercial reference probes and found to operate with equal or improved emf stability over a wide pH range and 3 orders of magnitude of different salt concentrations including potassium and sodium. The advantage being the lack of diffusion through the ionic semiconductor as compared with the diffusion through the porous separators of the commercial probes.

Type 2 membrane electrodes are found to be useful as reference electrodes in pH indication. As for example: a type two electrode can be constructed by coating a small piece of clean copper with a solution of 35% poly(ethylene oxide), supplied as Polyox C014 from Union Carbide and phenolic resin, supplied as 12704 from Durez as described in Example 9 above. After the solution has been dried and partially cured, it is coated with a second coat of the matrix Phenolic 12704, dried and both coats then cured. The coated copper type 2 membrane electrode can then be connected to a voltmeter with a Redox electrode such as platinum. Voltage readings for the type 2 electrode coupled with platinum in different pH solutions are:

| pH | 1 | 4 | 7 | 10 |
|---|---|---|---|---|
| Voltage | 0.830 | 0.530 | 0.460 | 0.359 |

The type 2 electrode has a slow response since the electrolyte is dependent upon equilibrium of the conduction hydrogel ions and the outer electrolyte and is not 'buffered' as with the electrolyte of the type 1 membrane electrode. The type 2 electrode has the advantage of small size and no maintenance.

EXAMPLE 39

A sensitive and stable measurement of free chlorine can made by using a noble metal and a type 1 or type 2 reference electrode as described above.

For example, a chlorine detector can be constructed using two copper wires with an active length of about 2 cm and a diameter of 0.3 cm. One of the wires is gold plated and the other is coated from a formulation such as 4 grams hydroxyethylcellulose or HEC as 'Cellosize' QP 100000-H as supplied by Union Carbide dispersed within 94 grams polyurethane dispersion or as 'NeoRez R-962' supplied by Polyvinyl Chemicals and water.

When the two copper wires are inserted within a water solution containing free chlorine, and connected to a voltmeter with an input impedance as low as 100k ohms, a sensitivity of over 150 mV/ppm at the 1 ppm level is obtained. The sensitivity being proportional to the log of the concentration of the chlorine or decreasing with increased chlorine concentration. Such a device has been found to operate continuously in swimming pools, hot tubs, spas and the like.

The following reaction is assumed to take place utilizing water splitting:

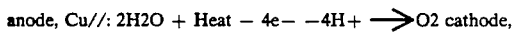

EXAMPLE 40

The above type 1 or type 2 probes can be used in voltage/current type measurements since the conductance of the junction is sufficiently high such that voltage drops across the membrane are generally negligible if low current densities are used.

For instance pH can be determined by using a type 1 membrane electrode filled with a buffered electrolyte of pH 1.00 and with a platinum electrode. The opposing electrode consists of another platinum electrode.

The two electrodes are inserted into the unknown analyte and connected to a reversible constant current source. The cell voltage is monitored as the current flows first with one polarity and then the other for fixed periods of time.

With a time interval of 1 minute, typical measured emfs for different pH samples are shown in Table 6.

TABLE 6

| Analyte pH | forward emf | reverse emf | emf difference |
|---|---|---|---|
| 10 | 2.341 | 1.677 | 0.664 |
| 7 | 2.420 | 2.185 | 0.235 |
| 4 | 2.064 | 2.182 | 0.118 |
| 1 | 1.614 | 1.571 | 0.043 |

The above yields the relationship: pH=11.5+3.35 * log(emf difference). Similar results can be obtained by using a type 2 platinum strip except that the type 2 may appear to have an inner basic rather than an acidic electrolyte.

EXAMPLE 41

The material of this invention can be used in electrochemical capacitors useful as filter capacitors or in supplying electrical power during short power outages. A capacitor was constructed using two platinum electrodes each with an area of 4 cm$^2$. These electrodes were initially separated by an anolyte and catholyte, each consisting of 30% Na2SO4, and a separating membrane made by coating a sheet of cellophane, as supplied by UCB film sector of Ghent, Belgium as 400 P Exp 389 unplasticised film, with a solution obtained by mixing and dispersing 15 parts by (dried) weight of hydroxyethyl cellulose obtained from Union Carbide Corporation as "Cellosize: QP 100,000-H in polyvinylidene chloride acrylate copolymer emulsion obtained from Unocal Chemicals as 76 RES 917.

After charging the capacitor to a voltage of 2.7 Volts, with a constant current of 19 mA, the pH of the anolyte was found to be about 1.7 while the catholyte was about 12. The charged electrochemical cell was then discharged into a load resistor of 1000 Ohms yielding the expected RC exponential voltage decay as given in Table 7.

TABLE 7

| Time | Voltage |
|---|---|
| 0.5 minutes | 1.27 Volts |
| 2 | 1.10 |
| 6 | 0.66 |
| 9 | 0.54 |

The magnitude of the total charge delivered into the load was unexpected, however, being equivalent to the charge delivered by a theoretical capacitor with a capacity of about 0.5 Farad. This extremely high capaci-

EXAMPLE 42

The materials of this invention can furnish a surface with a reduced sliding coefficient of friction or increased lubricity when wetted or hydrolyzed.

It is well known that hydrogels become slippery when wet. For instance poly(ethylene oxide) has been used to reduce the coefficient of friction between flowing water and a fire hose to increased the rate of transfer of water in fighting fires.

A friction reducing surface formed with a hydrogel is not, however, stable with time, i.e., the hydrogel will dissolve or leach out into the surrounding media.

The materials for this invention can present a lubricious hydrogel rich surface which is stable in time due to the dispersion of the hydrogels, which minimizes the formation of soluble gels, and the bonding of the hydrogels to the inert supporting matrix. The materials can be applied directly to the surface by standard methods such as calendaring, coextrusion or solvent coatings and the like. The surface to be coated can be prepared or primed for the applied lubricious coating or covering by first applying the matrix used in the final coating with reduced or no hydrogel content.

Such coatings should find application in liquid/solid interfaces where reduced friction is desired such as on hulls of boats, fire or water hose linings, pipe linings, liquid pumps and the like.

For example "guide wires" are used in medicine to guide catheters through the veins and arteries. Such wires have an inherently high coefficient of resistance which limits the depth and ease of penetration. It has been discovered that the lubricity can be considerably increased by coating the wire with 1) a prime coat of polyurethane resin supplied as HD-4610 supplied by C. L. Hauthaway & Sons Corporation and, after the prime coat has dried and cured, applying 2) a second coating of a solution obtained by mixing and dispersing 15 to 20 parts by (dried) weight of hydroxuethyl cellulose hydrogel obtained from Union Carbide Corporation as "Cellosize: QP 100,000-H into an emulsion of an abrasion resistant matrix such as a polyurethane resin supplied as HD-4610 supplied by C. L. Hauthaway & Sons Corporation.

While preferred embodiments of the present invention have been set forth for purposes of illustration, the foregoing description should not be deemed a limitation of the invention herein. Accordingly, various modifications, adaptations and alternatives may occur to one skilled in the art without departing from the spirit and scope of the present invention.

What is claimed is:

1. An electrochemical cell comprising:
   an anode;
   an anolyte;
   a cathode;
   a catholyte, the catholyte having a different pH when compared to the anolyte;
   a membrane separating said anolyte from said catholyte, said membrane comprising a nonporous solid composite material which is formed by a hydrogel substantially uniformly dispersed throughout an inert man made matrix material with said hydrogel comprising approximately 10 to 50% by weight of the dry composite material, ions selectively passing through said membrane from said anolyte to said catholyte whereby an electric current may flow through an external circuit connected between said anode and said cathode.

2. The cell of claim 1 wherein the pH difference between said anolyte and said catholyte has an absolute value of at least 1.0 pH.

3. The cell of claim 1 wherein anions selectively pass through said membrane from said anolyte to said catholyte and cations simultaneously selectively pass from said catholyte to said anolyte.

4. The cell of claim 1 wherein the matrix material is selected from the group consisting of polyvinylidene chloride, polyvinyl chloride, polyvinylidene fluoride, polyethylene, polypropylene, polyurethane, vinyl acetate/ethylene, and phenol formaldehyde.

5. The cell of claim 4 wherein the hydrogel is a synthetic material selected from the group consisting of polyethylene oxide, polyacrylic acid and polyacrylamide.

* * * * *